United States Patent
Taylor et al.

(10) Patent No.: US 12,156,913 B2
(45) Date of Patent: Dec. 3, 2024

(54) BIODEGRADABLE LIQUOGEL AND PH SENSITIVE NANOCARRIERS

(71) Applicant: NORTH CAROLINA CENTRAL UNIVERSITY, Durham, NC (US)

(72) Inventors: Darlene K. Taylor, Burlington, NC (US); Melony A. Ochieng, Durham, NC (US)

(73) Assignee: NORTH CAROLINA CENTRAL UNIVERSITY, Durham, NC (US)

( * ) Notice: Subject to any disclaimer, the term of this patent is extended or adjusted under 35 U.S.C. 154(b) by 766 days.

(21) Appl. No.: 17/072,804

(22) Filed: Oct. 16, 2020

(65) Prior Publication Data

US 2021/0177974 A1    Jun. 17, 2021

Related U.S. Application Data

(63) Continuation of application No. 13/818,782, filed as application No. PCT/US2011/050405 on Sep. 2, 2011, now abandoned.

(60) Provisional application No. 61/380,076, filed on Sep. 3, 2010.

(51) Int. Cl.
| | | |
|---|---|---|
| A61K 47/34 | (2017.01) | |
| A61K 9/00 | (2006.01) | |
| A61K 9/06 | (2006.01) | |
| A61K 31/4745 | (2006.01) | |
| A61K 31/565 | (2006.01) | |
| A61K 47/55 | (2017.01) | |
| A61K 47/59 | (2017.01) | |
| C08G 83/00 | (2006.01) | |
| C08L 101/00 | (2006.01) | |

(52) U.S. Cl.
CPC ............ *A61K 47/34* (2013.01); *A61K 9/0024* (2013.01); *A61K 9/06* (2013.01); *A61K 31/4745* (2013.01); *A61K 31/565* (2013.01); *A61K 47/551* (2017.08); *A61K 47/59* (2017.08); *C08G 83/006* (2013.01); *C08L 101/005* (2013.01)

(58) Field of Classification Search
CPC ...................................................... A61K 47/34
See application file for complete search history.

(56) References Cited

U.S. PATENT DOCUMENTS

2008/0200434 A1* 8/2008 Daniloff ................. A61K 31/69
514/64

* cited by examiner

*Primary Examiner* — Carlos A Azpuru
(74) *Attorney, Agent, or Firm* — LADAS & PARRY LLP

(57) ABSTRACT

A delivery system using materials that form a liquogel or nanocarrier are described. The delivery system comprises hyperbranched polyglycerols (HPGs). The delivery system can include a drug or therapeutic agent and this system can be used to administer the drug or therapeutic agent locally. The delivery system provides for controlled release of the drug or therapeutic agent.

11 Claims, 25 Drawing Sheets

10°C         24°C         35°C

Visual observation of gel process

Optical absorption a function of temperature observation of nanogel transition temperature.

Differential Scanning Calorimetry (DSC) curve showing transition in nanogel at 35.7°C. Heating rate, 10°C/min.

BIODEGRADABLE LIQUOGEL AND PH SENSITIVE NANOCARRIERS

RELATED APPLICATION

This application is a continuation of U.S. application Ser. No. 13/818,782 filed on Feb. 25, 2013, which is an application under 35 U.S.C. 371 of International Application No. PCT/US2011/50405 filed on Sep. 2, 2011, which claims priority from U.S. Application No. 61/380,076 filed on Sep. 3, 2010, the disclosures of which are incorporated in their entirety by reference herein.

This invention was supported in part by funds from the U.S. Government NIH/ORWH BIRCWH 5 K12 HD043446-04, NIH 5-G11-HD041831-05 EARDA and DMR-0959679. The U.S. government may therefore have certain rights in the invention.

FIELD OF THE INVENTION

The present invention relates to a temperature responsive liquogel and pH sensitive nanocarriers.

BACKGROUND OF THE INVENTION

For treatment of certain diseases and conditions, systemic therapy does not necessarily provide therapeutic tissue levels of a drug. It may also result in deleterious effects in the patient. As such there is a need for a local delivery system that can be used to deliver a drug or therapeutic agent locally to a specific site.

A number of synthetic hydrogels with a lower critical solution temperature (LCST) below body temperature have been touted as promising injectable drug delivery systems [1-7]. Hydrogels are often used in biological applications thus they are often biomaterials. Hydrogels swell in water and typically undergo a phase transition to gel immediately after reaching their LCST. Viable representatives of these polymers are thermally smart and include polysaccharide derivatives [8], poly(N-isopropylacrylamide) (PNIPAAm) [9-11], and poly(ethylene glycol) (PEG) [6, 8]. However, all of these representative thermally smart polymers include hydrophilic materials that are biologically non-degradable on any useful timescale. Biodegradable macromers such as hydrophobic lactides are often copolymerized with thermogelling polymers to facilitate bioadsorption and clearance from the body at physiological temperatures [12]. PNIPAAm-based hydrogels incorporating poly(lactic acid) (PLA) macromers are routinely investigated as injectable bulking biomaterials since the ester linkages of PLA are hydrolytically degraded in the presence of water and the LCST can be tuned by the monomer feed ratio. Further improvements to the hydrogel delivery system are realized by copolymerizing small amounts of hydrophilic molecules, such as acrylic acid, to enhance the bioadsorption of the hydrolytically degraded copolymer [13]. Although the copolymers discussed above represent feasible options for developing in situ gelling biomaterials-indeed a prototype PNIPAAm-based delivery system has been used in animal models with compromised ventricular architecture of the heart [9], limitations exist with respect to extending the utility of one delivery system to more than one application. No ideal drug delivery system has been designed to date.

There is a need for a delivery system that includes degradable biomaterials that not only respond to temperature but also easily accommodate chemical linkage of active molecules. Such a platform could utilize orthogonally triggered mechanisms (such as temperature stimulated entrapment and pH programmed linkage) to provide targeted and controlled delivery of therapeutic agents. The present invention relates to multi-functional and programmable delivery systems for targeted therapy. Local delivery of drugs embedded in a hyperbranched polyglycerol (HPG) based nanocarrier has the potential to reduce the need for surgical and other procedures that are time consuming for the patient and can result in complications to the patient.

According to this invention thermoresponsive, biocompatible nanocarriers have been designed and synthesized to contain various amounts of HPG.

SUMMARY OF THE INVENTION

The present invention relates to a delivery system using materials that form a liquogel comprising hyperbranched polyglycerols (HPG).

Another aspect of the invention is a pH sensitive nanocarrier prepared using hyperbranched glycerols and a pH responsive linker.

According to another aspect of the invention, the delivery system comprises a drug or therapeutic agent that is entrapped in a liquogel or nanocarriers.

Another aspect of the invention is a method of using the delivery system to administer a subject a drug or therapeutic agent locally.

DEFINITIONS

Figure 1:
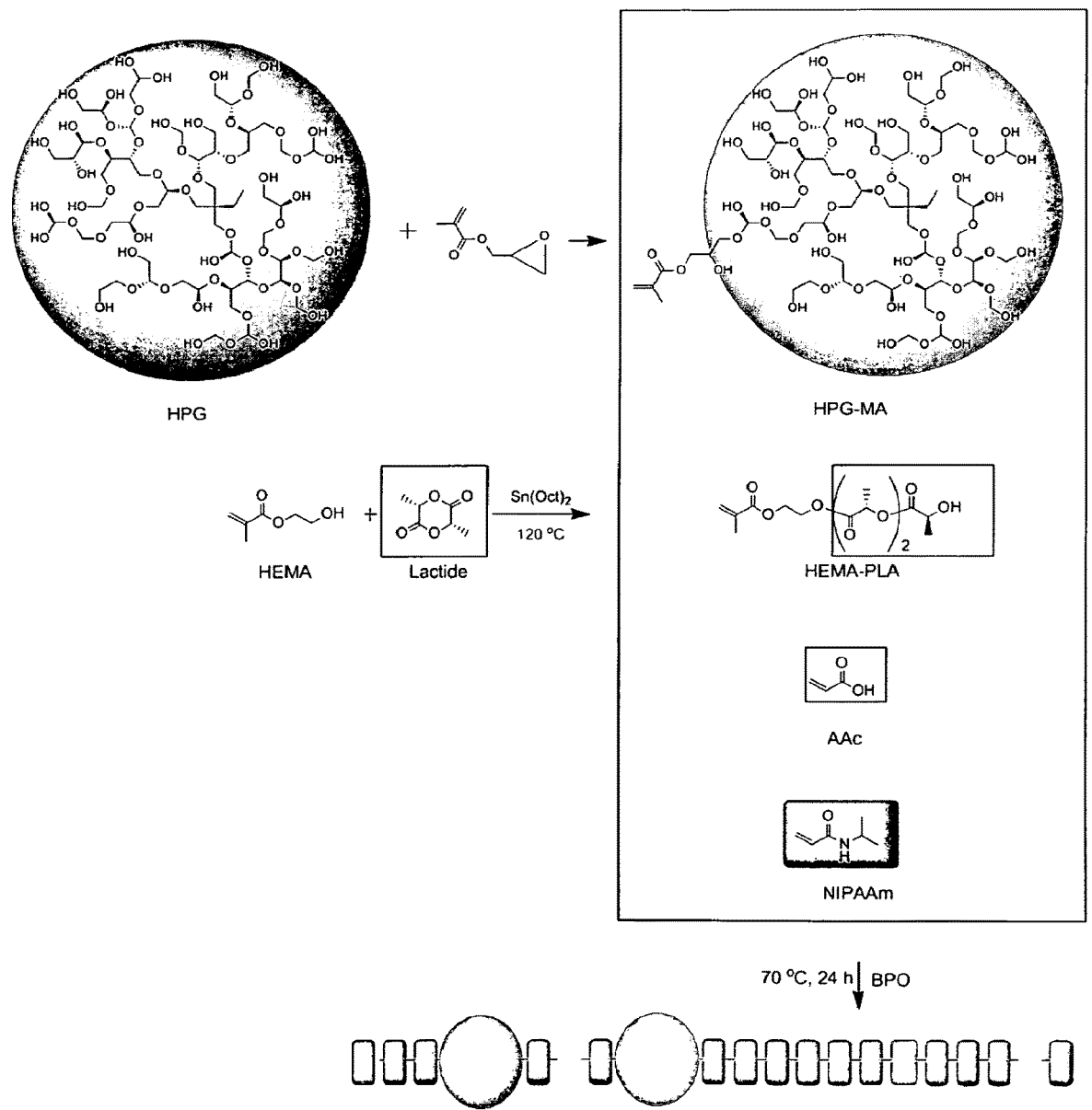
FIG. 1 shows a schematic for obtaining thermogelling biomaterials from acrylic macromers methacrylated-hyperbranched polyglycerol (HPG-MA) and 2-hydroxyethyl methacrylate-poly(lactic acid) (HEMAPLA) copolymerized with monomers n-isopropylacrylamide (NIPAAm) and Acrylic Acid (AAc) by Radical Polymerization.

Listed below are definitions, which apply to the terms as they are used throughout the specification (unless they are limited in specific instances).

As used herein "drug or therapeutic agent means a diagnostic or therapeutic molecule that can be used for prevention or treatment of a disease, condition or disorder. As used herein the terms "drug or therapeutic agent" can be used interchangeably and the liquogels and nanocarriers of this invention may contain one or more drugs, or therapeutic agents.

As used herein the term "liquogel" is a material that transitions from liquid to gel due to a change in temperature.

As used herein the term "orthogonal trigger" means external stimuli (i.e. temperature trigger, pressure trigger, magnetic trigger, electrochemical trigger etc.) that illicit independent responses from the material.

As used herein the term "physiologically acceptable" is meant that the carrier, diluent, and/or excipients, must be compatible with the other ingredients of the formulation, and not deleterious to the recipient thereof "Physiologically acceptable" also means that the compositions, or dosage forms are within the scope of sound medical judgment, suitable for use for an animal or human without excessive toxicity, irritation, allergic response, or other problem or complication, commensurate with a reasonable benefit/risk ratio.

As used herein "prevention" refers to delaying, slowing, inhibiting, reducing or ameliorating the onset of disease or condition.

As used herein, the terms "treatment" and "therapy" and the like refer to alleviating, slowing the progression, prophylaxis, attenuation or cure of existing disease or condition. "Treatment" of a subject includes the application or administration of a composition to a subject, or application or administration of a composition to a cell or tissue from a subject who has such a disease or condition, or is at risk of or susceptible to such a disease or condition, with the purpose of curing, healing, alleviating, relieving, altering, remedying, ameliorating, improving, or affecting the disease or condition, the symptom of the disease or condition, or the risk of or susceptibility to the disease or condition.

As used herein the term "subject" means mammals. Examples of mammals include humans, monkeys, cows, sheep, goats, dogs, cats, mice, rats, and transgenic species thereof.

DETAILED DESCRIPTION OF THE INVENTION

The biodegradable liquogel of this invention responds to temperature and can easily accommodate chemical linkage of active molecules such as drugs and therapeutic agents. This system can utilize orthogonally triggered mechanisms to provide targeted and controlled delivery of a drug or therapeutic agent.

In an aspect of the invention thermoresponsive, crosslinking, and biodegradable macromers are copolymerized with hyperbranched polyglycerols (HPG) to form a composition that can be used to incorporate or entrap a drug, other therapeutic agent or one or more of both. In some aspects of the invention the biodegradable and thermoresponsive copolymers are covalently linked with HPG macromers that can be further manipulated by an orthogonal trigger.

The compositions of this invention are soluble in aqueous media and form liquogels. The nanocarrier will gel at body temperature. Gelation properties have been optimized by systematically varying the ratios of the components of the nano carrier. The in vitro degradation kinetics have been evaluated, and the cytotoxicity of gradation products have been evaluated on cultured cells. The copolymers presented herein represent a tunable thermoresponsive platform with potentially versatile functionality for drug delivery. The incorporation of HPG macromers permits chemically modifiable functional sites. HPG macromers impart functionality to the copolymers because of the internal cavities that form that are suitable for small molecule interaction, large number of modifiable surface hydroxyl groups, and excellent biocompatibility [14-20]. In addition this domain with mostly unaltered hydroxyl groups is available for additional modification of moieties that are orthogonally exploited by a trigger other than temperature has been developed. Other triggers include pH triggers, pressure triggers, magnetic triggers, and electrochemical triggers. The liquogel provides a sufficient barrier against metabolic degradation and allows solubility of the drug therapeutic agent. The liquogel gels in vivo before degrading in a controlled way to release the entrapped drug or therapeutic agent. The drug may be entrapped non-covalently or by hydrogen bonding. The release can be controlled by one or more orthogonal external triggers. Over time, for example, in a liquogel that includes ester linkages, these linkages are hydrolyzed and as they break down, the pore size of the matrix increases to facilitate release of the entrapped drug or therapeutic agent from the matrix of the liquogel. The localized release of the drug or therapeutic agent helps to prevent systemic side effects. Local delivery of such agents allows the delivery of intact molecules and can treat the decease or condition while avoiding systemic side effects.

The liquogel is in solution at temperatures ranging from 5° C. to 27° C. and gels at body temperature before degrading to release an entrapped drug or therapeutic agent.

A method to yield a series of copolymers with different ratios of NIPAAm, HEMAPLA, AAc, and HPG-MA is described herein. The liquogels typically have an LCST between room temperature and 37° C.

A pathway to prepare HPGs was recently reported by Sunder et al [21]. based on the anionic polymerization of a latent $AB_2$-type glycidol monomer using ring-opening multibranching polymerization (ROMBP). Addition of the $AB_2$-type glycidol monomer permits its reactivity with the growing multifunctional hyperbranched polymer, leading to well-defined growth of the macromolecules. A rapid proton exchange equilibrium maintains all hydroxyl groups present as potentially active propagation sites, thus leading to random, but controlled, branching. Other polymer approaches [22-23] cannot easily provide these properties without significant increases in the number of synthetic steps and the cost of synthesis. Thus, HPGs may now be obtained in a single step with properties that rival the dendritic materials platform [24].

In one aspect of this invention, the liquogel nanocarrier comprises HPG macromers, a crosslinker, a biodegradable component, and a thermoresponsive component. Systematically varied ratios of HPG macromers, crosslinker, biodegradable component and thermoresponsive component can be used to prepare liquogels. This can result in liquogels having different properties. The liquogel nanocarrier will gel at body temperature. Thermoresponsive, biocompatible liquogels with various amounts of HPG (-up to 17 wt %) have been generated. Gelation properties have been optimized by systematically varying the ratios of the components of the liquogel. The composition of each component in the liquogel determines the lower critical solution temperature (LCST) of the liquogel. At a temperature less than the LCST, the liquogel is a liquid and can be physically mixed with a drug or therapeutic agent to form a suspension. When the temperature is increased above the LCST, the liquogel gels and retains a shape that will entrap or incorporate the drug or therapeutic agent within its matrix. In most cases, the drug or therapeutic agent are non-covalently or hydrogen bonded in the liquogel.

The in vitro degradation kinetics of these liquogel have been evaluated, and the cytotoxicity of degradation products have been evaluated with cultured cells.

In an aspect of the invention the crosslinker is an acrylate group. A nonlimiting example of an acrylate group is hydroxyethyl methacrylate (HEMA).

Non limiting examples of compounds that can be used as the biodegradable component are poly(lactic acid) (PLA), lactide, poly(trimethylene carbonate), and poly(ε-caprolactone). Other examples of compounds that can be used as the biodegradable component are hyaluronic acid, gelatin, peptides, and collagen. Poly(lactic acid) (PLA) provides biodegradability through hydrolytic bond cleavage.

Non limiting examples of compounds that can be used as a thermoresponsive component are N-alkyl acrylamide or polyethylene glycol. The alkyl is a straight, branched or cyclic C1-C6 alkyl. Non-limiting examples of such alkyl groups are methyl, ethyl, n-propyl, isopropyl or cyclopropyl.

A non-limiting example of an N-alkyl acrylamide is N-isopropylacrylamide (NIPAAm). Poly N-isopropylacrylamide is represented by PNIPAAm.

A non limiting example of a hydrophilic compound that can be used to re-solubilize the degraded polymer products is acrylic acid (AAc). AAc provides a hydrophilic component to increase the transition temperature of the copolymer after hydrolysis.

According to another aspect of the invention, the liquogel is prepared from at least: N-isopropylacrylamide or an N-alkyl acrylamide in which the alkyl is methyl, ethyl, propyl, isopropyl or cyclopropyl; acrylic acid and/or methacrylic acid, an acrylic monomer having an amine-reactive group (such as acrylic N-hydroxysuccinimide ester) and a polyester macromer. For example and without limitation, the polyester macromer is a polylactide macromer, comprising hydroxyethyl methacrylate residues and varying numbers of lactide units/residues.

Figure 12:
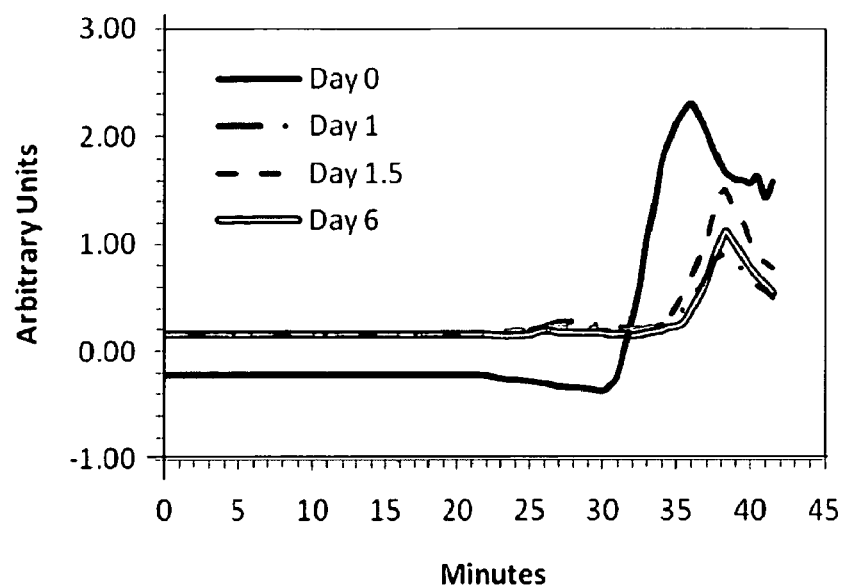
FIG. 12 shows degradation studies of 16.7% copolymer gel HPG High at 37° C. showing GPC curves (A) and change in molecular weight with time (B).
Figure 12:
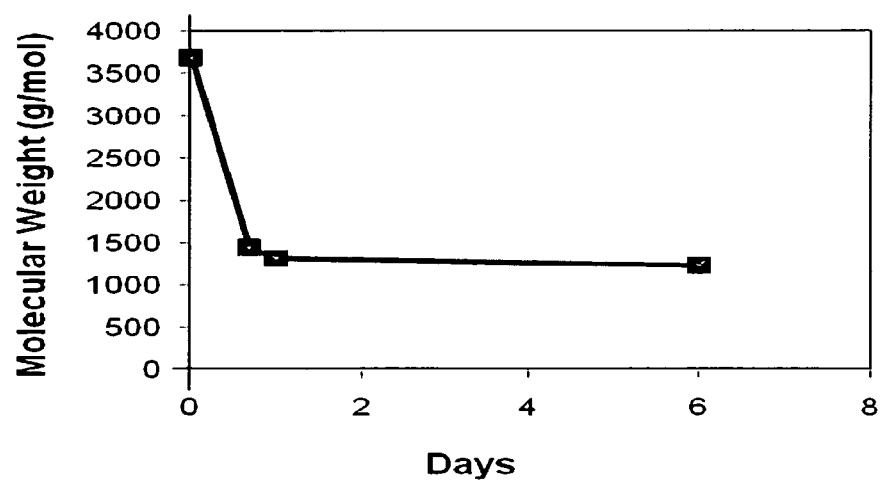

In an aspect of the invention, acrylic acid, lactide, N-isopropylacrylamide, hydroxyethylmethacrylate and hyperbranched polyglycerol (HPG) macromer units are used to prepare the liquogels. FIG. 1 shows a HPG based liquogel with a HPG multifunctional platform, functional acrylate groups that comprise the crosslinker, biodegradable group and thermoresponsive and acrylic acid groups). A multifunctional macromer, methacrylated hyperbranched polyglycerol (HPG-MA) with an average of 1 acrylate unit per copolymer, was synthesized and copolymerized with N-isopropylacrylamide (NIPAAm), hydroxyethyl methacrylate-polylactide (HEMA-PLA), and acrylic acid (AAc). The resulting product, Poly(NIPAAm-co-HEMAPLA-co-AAc-co-HPG-MA) displayed increasing lower critical solution temperatures (LCST) as the HPG content increased over a range of macromer ratios. For the copolymer with the maximum HPG incorporation (17% by weight), the LCST was ~30° C. In addition, this nanocarrier showed no toxicity when human uterine fibroid cells were co-cultured with the copolymer for up to 72 h. This copolymer lost approximately 92% of its mass after 17 hours at 37° C. (FIG. 12).

Figure 2:
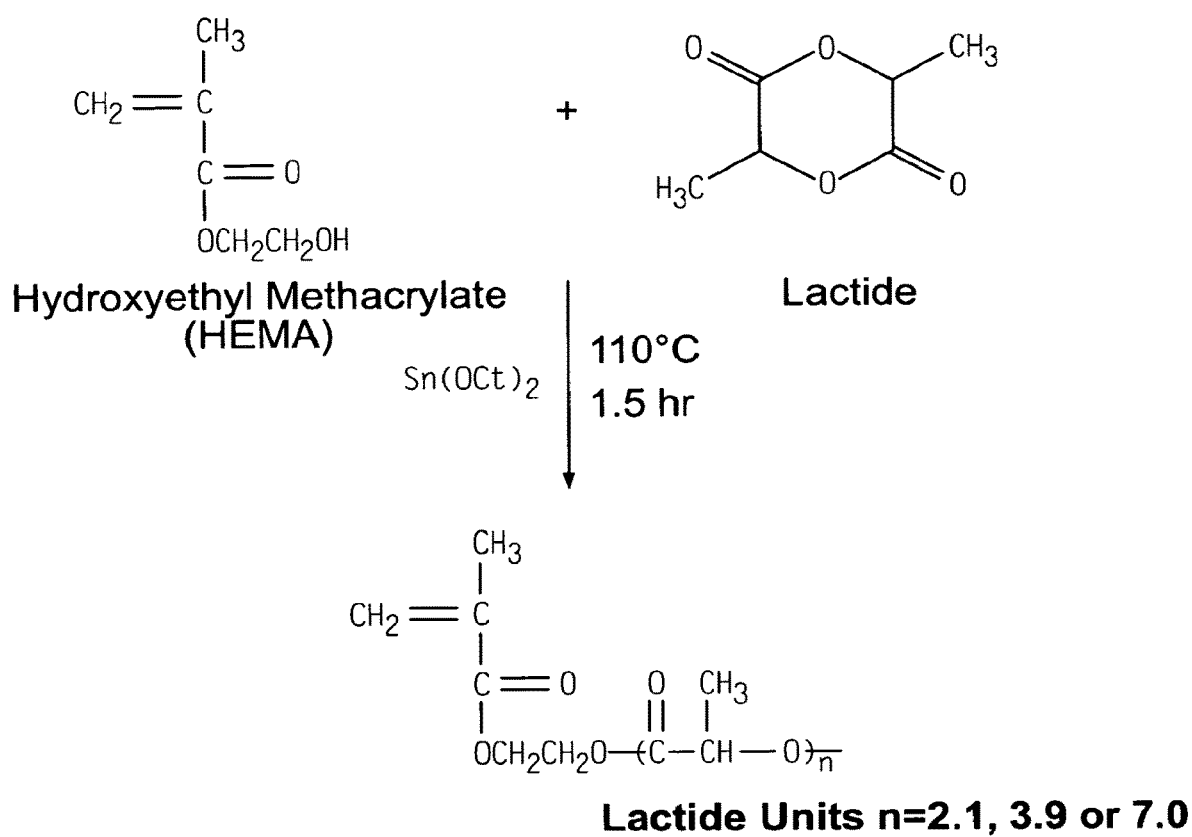
FIG. 2 shows a method according to U.S. Patent Publication 2008/0096975 and is a schematic drawing for the synthesis of the polylactide hydroxyethyl methacrylate-lactide (HEMAPLA) macromer from hydroxyethyl methacrylate (HEMA) and lactide (LA).

Other non limiting examples of components that can be used with HPGs are the components disclosed in US Patent application publication 2008/0096975 (Guan et al.) and include compositions comprising an N-isopropylacrylamide residue (an N-isopropylacrylamide monomer incorporated into a polymer), one or both of an acrylic acid residue and a methacrylic acid residue and an acrylic residue. (See FIG. 2).

The HPG polymers may be functionalized with an optimized combination of lactides, methacrylates, and isopropylacrylamides to afford a degradable, vitrifing and thermoresponsive delivery system.

Each component plays a specific role in the resulting copolymer. In an aspect of the invention N-isopropylacrylamide (NIPAAm) provides thermogelling with a LCST below physiological conditions, poly(lactic acid) (PLA) provides biodegradability through hydrolytic bond cleavage, acrylic acid (AAc) provides a hydrophilic component to increase the transition temperature of the copolymer after hydrolysis, and HPG provides a number of hydroxyl groups available for attachment of drug or therapeutic agent or chemical modification to covalently attach fluorescent tags for biomarkers or pH triggered linkers terminated with bioactive molecules.

In an aspect of the invention, HEMA-PLA was chosen over PLA alone to facilitate chemical synthesis. HPG, in like manner, was functionalized with methacrylate groups, HPG-MA, in order to realize its incorporation in the copolymer.

In an aspect of the invention, the PLA macromer is incorporated as side components linked to 2-hydroxyethyl methacrylate (HEMA), yielding HEMA-PLA. HEMA is easily coupled to PLA and renders an olefin group that can be copolymerized with the other acrylic macromers.

The liquogel nanocarriers and compositions of the invention can be prepared by co-polymerizing the components by any useful polymerization method, for example, and without limitation by free-radical polymerization or ring-open polymerization. In addition to these methods and the method shown in FIG. 1 can be prepared by other methods known to those of skill in the art.

Methacrylated HPGs have been incorporated into thermoresponsive hydrogels creating materials with added functional groups that can be easily manipulated in the design of drug delivery systems. The copolymers were loaded with HPG up to 17% molar equivalents and displayed LCST as high as 30° C. for the highest HPG containing copolymer. All of the transition temperatures observed for the copolymers of the examples were below physiological temperature of 37° C., and increasing the feed ratio of HPG beyond 17% molar equivalents or % by weight would presumably further increase the sol-gel temperature. The selected poly(NIPAAm-co-HEMAPLA-co-AAc-co-HPG-MA) at a molar ratio of 70:1:3.3:17 has attractive properties and was not toxic to cultured uterine fibroid cells.

The LCST can be determined by measuring the change in transmittance with a UV-Vis spectrometer as a function of temperature (Advanced Drug Delivery Reviews (1998), 31: 197-221 and Annals N.Y. of Science, 1999, 875(1):24-35). LCST also can be determined by any other method known in the art-for example and without limitation by Differential Scanning calorimetry (DSC).

The copolymers can be characterized by nuclear magnetic resonance (NMR) spectroscopy and gel permeation chromatography (GPC). Solutions of the macromers were characterized for their phase-transition properties by differential scanning calorimetry (DSC) and optical absorption. Copolymers were analyzed by mass spectrometry and cytocompatibility and degradation properties were also assessed.

Synthesis of HPG-MA

The multifunctional, degradable thermoresponsive copolymer HPG-MA was synthesized in three steps as depicted in FIG. 1. FIG. 1 shows the preparation of thermogelling biomaterials from the acrylic macromers methacryalated-hyperbranched polyglycerol (HPG-MA) and 2-Hydroxyethyl Methacrylate-poly(lactic acid) (HEMAPLA) copolymerized with monomers N-Isopropylacrylamide (NIPAAm) and acrylic Acid (AAc) by radical polymerization. Methacrylate moieties that enable incorporation of HPG into the copolymer are introduced in the first step. The schematic illustration of this reaction is simplified, recognizing that on average one out of 29 pendant HPG hydroxyl groups reacted in the methylation step. The HEMAPLA macromer is prepared as a stand alone reaction. The resulting four component copolymer is a branched statistical copolymer.

The first reaction depicted in FIG. 1 is a method used to prepare methacrylated HPG macromer. The methacryloyl group was directly linked to the starting HPG by transesterification. $^1$H NMR analysis of the product was consistent with results reported by Oudshoorn et al. [26]. In addition to the four methylene and one methine (broad multiplet at 3.4 ppm) and one hydroxyl proton (4.8 ppm) originating from the monomer repeat units of HPG, new peaks were detected. $^1$H NMR spectra shown in FIG. 3A shows the $^1$H NMR spectra ($CD_3OD$) of hyper branched polyglycerol (HPG) obtained from anionic polymerization initiated with 1,1,1-tris(hydroxymethyl)propane. FIG. 3B is the $^1$H NMR spectra (DMSO-$d_6$) of methacrylated HPG (DS=0.16) (FIG. 3C); shows the magnified region where the acylate peaks of HPG-MA appear and confirmed the incorporation of the methacryloyl group with the observation of methyl (1.8 ppm) and acrylate protons (5.67 and 6.08 ppm, shown more clearly with the enlarged insert). Integration of the peak areas for these acrylate protons relative to the HPG [terminal hydroxyl] protons suggests that the fraction of HPG macromer derivatized with methacrylate groups to yield HPG-MA was 0.16. This low degree of conversion implies that the HPG is mostly unaltered but when substitution does occur on average ~1 out of 29 hydroxyl groups of HPG were substituted with a methacryloyl group.

Figure 4:
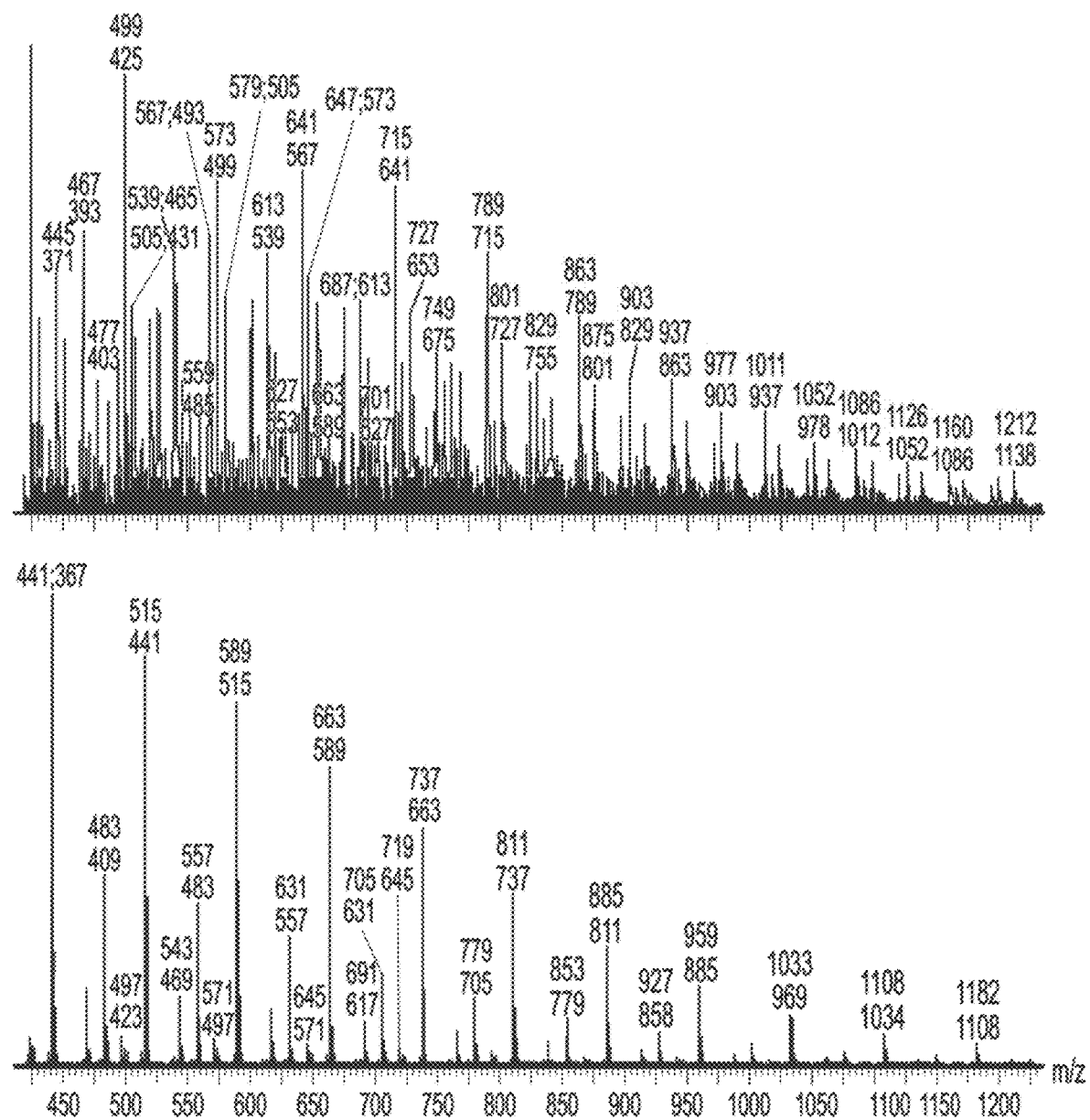
FIG. 4 shows ESI-TOF of (A) HPG-MA and (B) HPG macromer precursor.

MALDI-TOF was used to determine the mass of HPG-MA ($M_n$=1,253 g/mol, $M_w/M_n$=1.13, data not shown). The MALDI MS of HPG-MA was consistent with the ion fragmentation pattern obtained by ESI MS which is shown in FIG. 4A. The top mass number in the figure corresponds to the peak m/z value, with a charge (z) of +1 evident in all labeled peaks (data not shown). The bottom mass number (FIG. 4B) represents a delta mass of 74 from the peak m/z value, corresponding precisely to the repeat unit mass of the $C_3H_6O_2$ interval (glycidol, MW=74). There are two significant series of peaks that differ by mass unit 74 within their respective series (m/z= . . . 499, 573, 647, 721 . . . and m/z=641, 715, 789, 863 . . . ). The mass difference between the two series (i.e. 641 minus 499 or 715 minus 573, etc.) equals 142, corresponding precisely to the mass of one methacrylated glycidol unit (MW=142).

Figure 3:
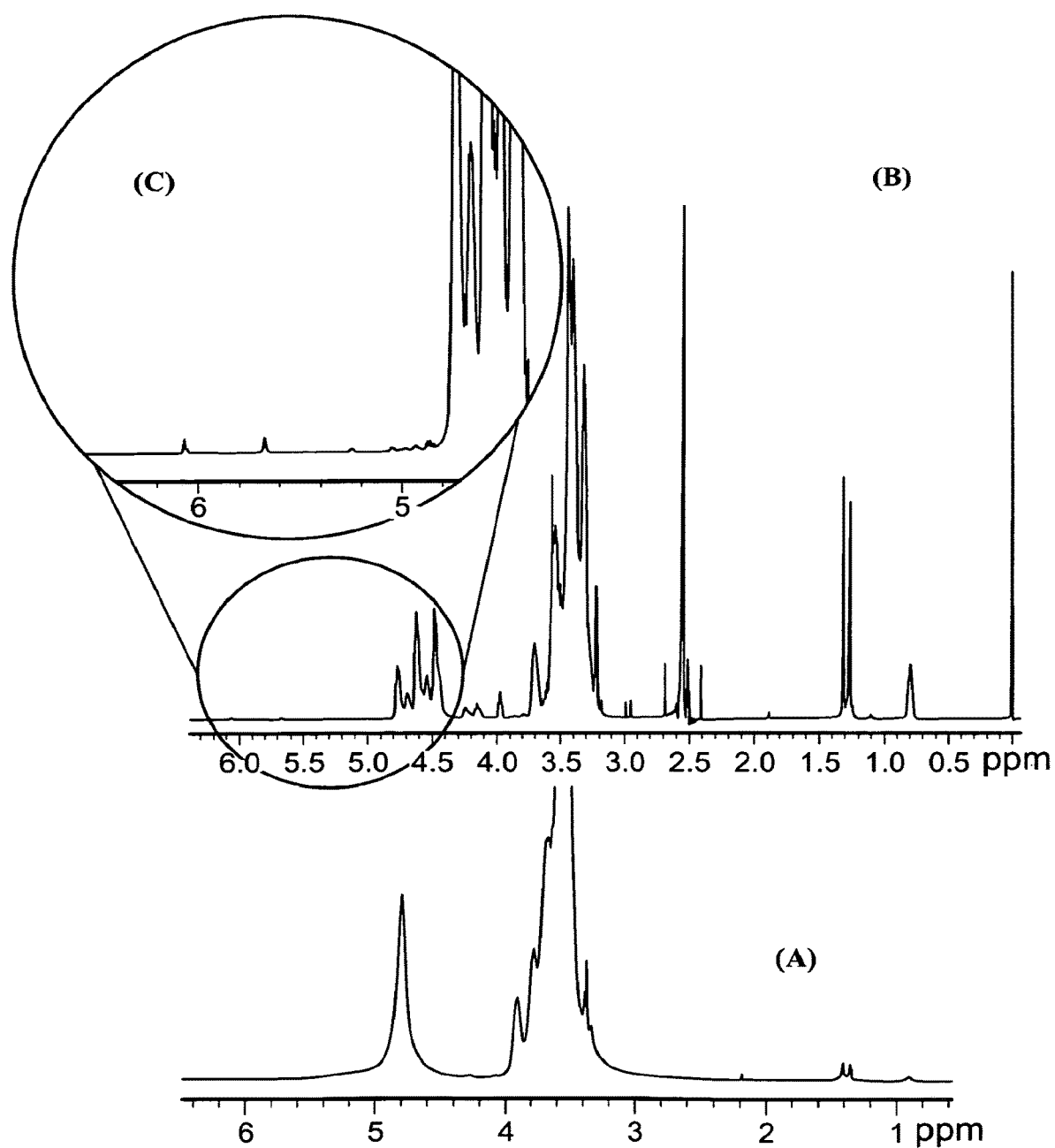
FIG. 3 shows $^1$H NMR spectra ($CD_3OD$) of hyperbranched polyglycerol (HPG) obtained from anionic polymerization initiated with 1,1,1-tris (hydroxymethyl)propane.

These results suggest that only one methacryloyl group is incorporated into HPG-MA, consistent with data collected using $^1$H NMR (FIG. 3). Observing two major ion series is consistent with the expected polydispersed copolymer population. For instance, because in this embodiment most of the polymer chains in HPG share the same initiator (1,1,1-tris (hydroxymethyl)propane), the mass distribution among dispersed macromers would vary by a multiple of 74 dependent on the number of glycidol monomers. Thus, mass spectrum analyses of the dispersed macromers would yield superimposed peaks that vary by m/z=74 following the loss of glycidol monomers during ESI. The only variation to superimposition detected resulted from the loss of one mass of 142, instead of 74, suggesting some copolymer fragments contain one methacrylated glycidol while others do not. No evidence of multiple methacryloyl incorporation was observed. For comparison, FIG. 4B shows the precursor HPG macromer with three major series of molecular weight distributions having a repeat unit mass m/z=74 within the series (m/z=499, 573, 647 . . . ; m/z=527, 601, 675; and m/z=559, 633, 707 . . . ). The difference between these series as shown in FIGS. 4A and 4B may correspond to incorporation of a cyclic derivative of glycidol as previously reported [21]. No peaks are observed in HPG with a mass delta of 142. Together, this data confirms that glycidyl methacrylate was incorporated into the hyperbranched structure. No evidence of multiple methacryloyl incorporation was observed. This supports $^1$H-NMR data discussed above, which implied that on average ~1 out of 29 hydroxyl groups of HPG are substituted with a methacryloyl group.

Synthesis of HEMAPLA

Figure 5:
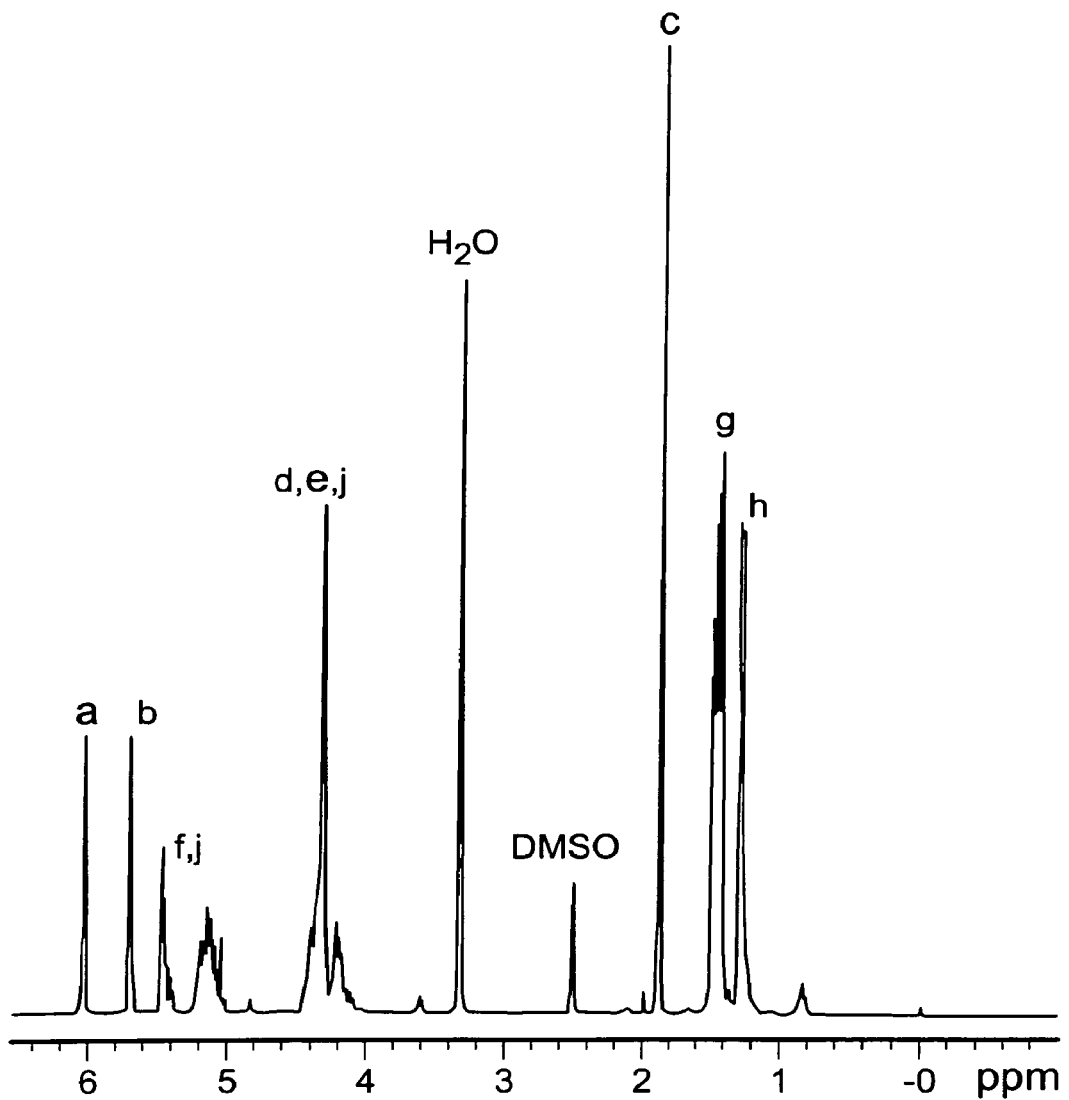
FIG. 5 shows $^1$H NMR spectra (DMSO-$d_6$) of HEMAPLA.
Figure 5:
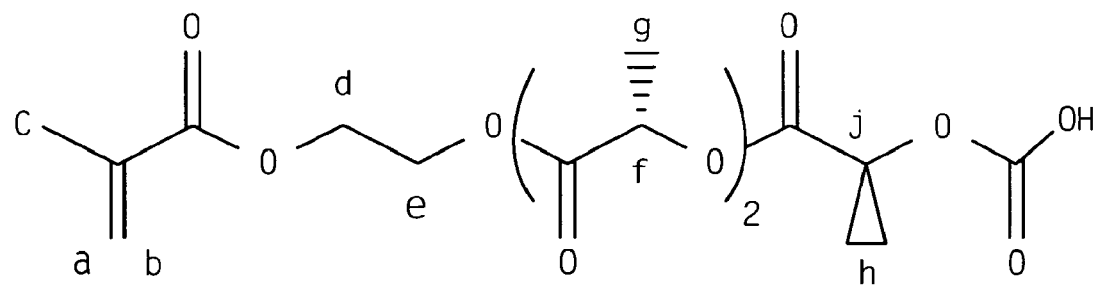

Prior to the copolymer polymerization, the macromer HEMAPLA was prepared and its synthesis confirmed by $^1$H NMR shown in FIG. 5 which is $^1$H NMR spectra (DMSO-$d_6$) of HEMAPLA.

The proton peaks are in agreement with the molecular structure of HEMAPLA. The number average length of PLA units per macromer was determined from the $^1$H NMR spectrum by calculation from the ratio of the integrals of hydrogen peaks from PLA (peaks c, f, j, and h) relative to the double bond hydrogen peaks (peaks a and b at 5.6 and 6.1 ppm). A PLA repeat unit of 3 was determined and found to be in agreement with the molar feed ratio of HEMA to L-lactide (1:1) utilized in the synthesis of HEMAPLA Synthesis of Copolymers A series of copolymers with different relative molar amounts of HPG-MA were prepared by free radical polmerization. The low degree of methacrylate substituted hydroxyl groups ([an average of] 1 out of 29 groups) ensured that on average only one link occurred between the polymer backbone and the incorporated HPG macromer. This degree of substitution also minimizes the probability of HPG initiated crosslinks in the final copolymer products. Any HPG-MA not incorporated into the copolymer was isolated and removed during the workup. The four component copolymers were synthesized with different monomer and macromer feed ratios and their properties are summarized in Table 1.

HPG content in each copolymer, the water signal was negated by comparing the relative ratio of $H_2O$:DMSO signal (2.5 ppm) in the control sample to the $H_2O$:DMSO in each of the respective copolymers. Using this approach, the signal at 3.4 ppm more closely reflects the approximate HPG content. The monomer compositions in the copolymers were found to be similar to the feed ratios as shown in Table 1.

The molecular weights of the poly(NIPAAm-co-HEMA-PLA-co-AAc-co-HPG-MA) copolymers were determined by GPC. The molecular weights obtained for the synthesized copolymers were low due to the monomer to initiator feed ratio. The molecular weight decreases as the HPG-MA feed ratio content increases. This result may be a result of steric hindrance as it is more difficult to easily incorporate the

TABLE 1

Characteristics of poly(NIPAAm-co-HEMAPLA-co-AAc-co-HPG-MA) copolymers with different HPG feed ratios.

(NIPAAm|HEMAPLA|AAc|HPG-MA)

| Sample ID | Yield | Feed Ratio | 1H NMR ($M_n$) | GPC $M_n$ | $M_w/M_n$ | LCST (° C.)[a] |
|---|---|---|---|---|---|---|
| HPG High | 88% | (80|10|1|9) | (79|1|3.3|17) | 3689 | 1.7 | 28 ± 0.1 |
| HPG Med | 83% | (86|7|1|6) | (85|8|0.8|6) | 3455 | 1.7 | 24 ± 0.2 |
| HPG Low | 87% | (85|10|1|4) | (85|11|0.2|4) | 4465 | 1.5 | 22 ± 0.1 |
| Control | 90% | (87|10|3|0) | (86|12|1.8|0) | 1253 | 1.5 | 20 ± 0.4 |

Figure 6:
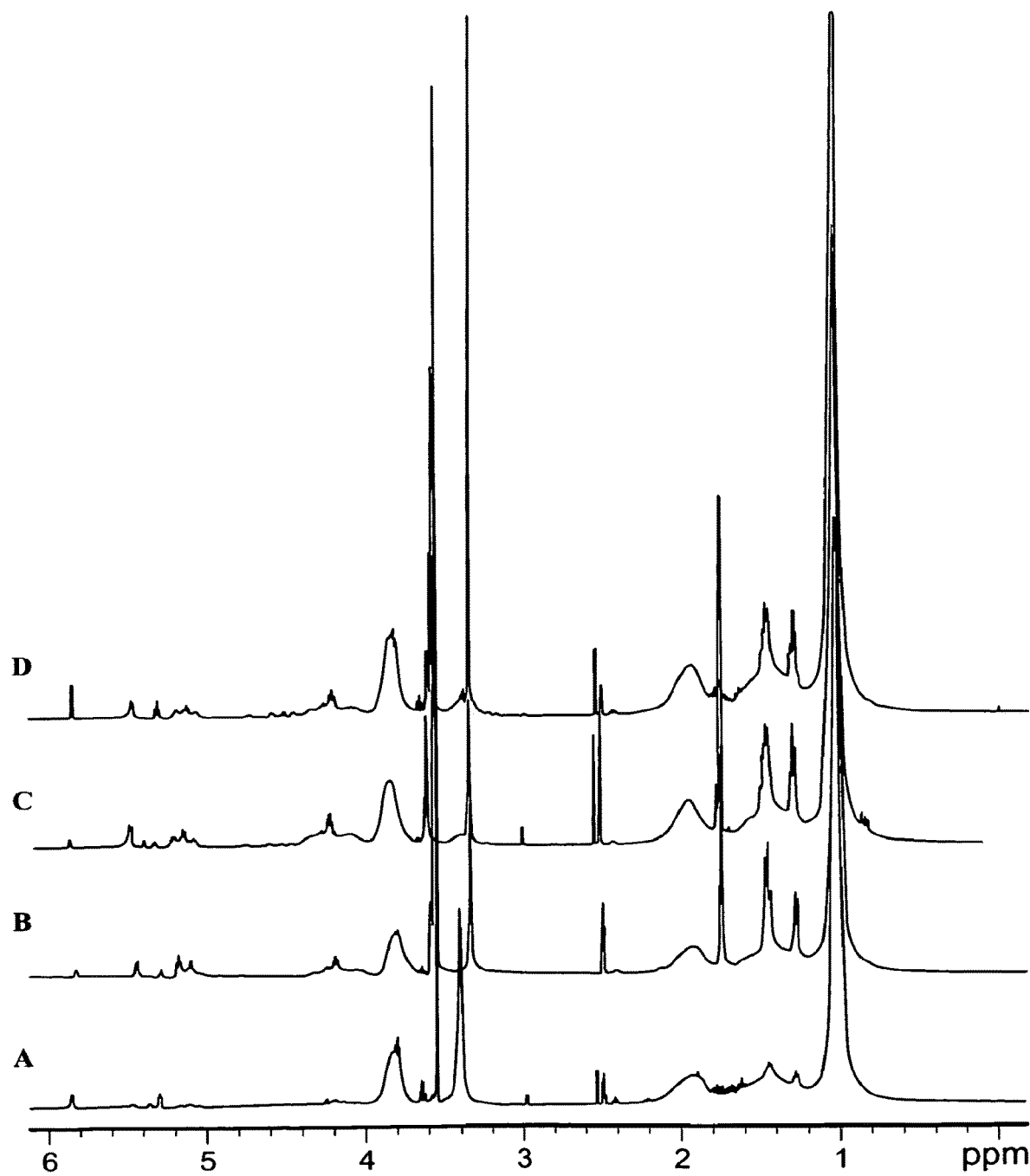
FIG. 6 shows $^1$H NMR spectra (DMSO-$d_6$) of copolymers of poly(NIPAAm-co-HEMAPLA-co-AAc-co-HPG-MA), where the spectra represent (A) Control; (B) HPG Low; (C) HPG Med; and (D) HPG High.
Figure 7:
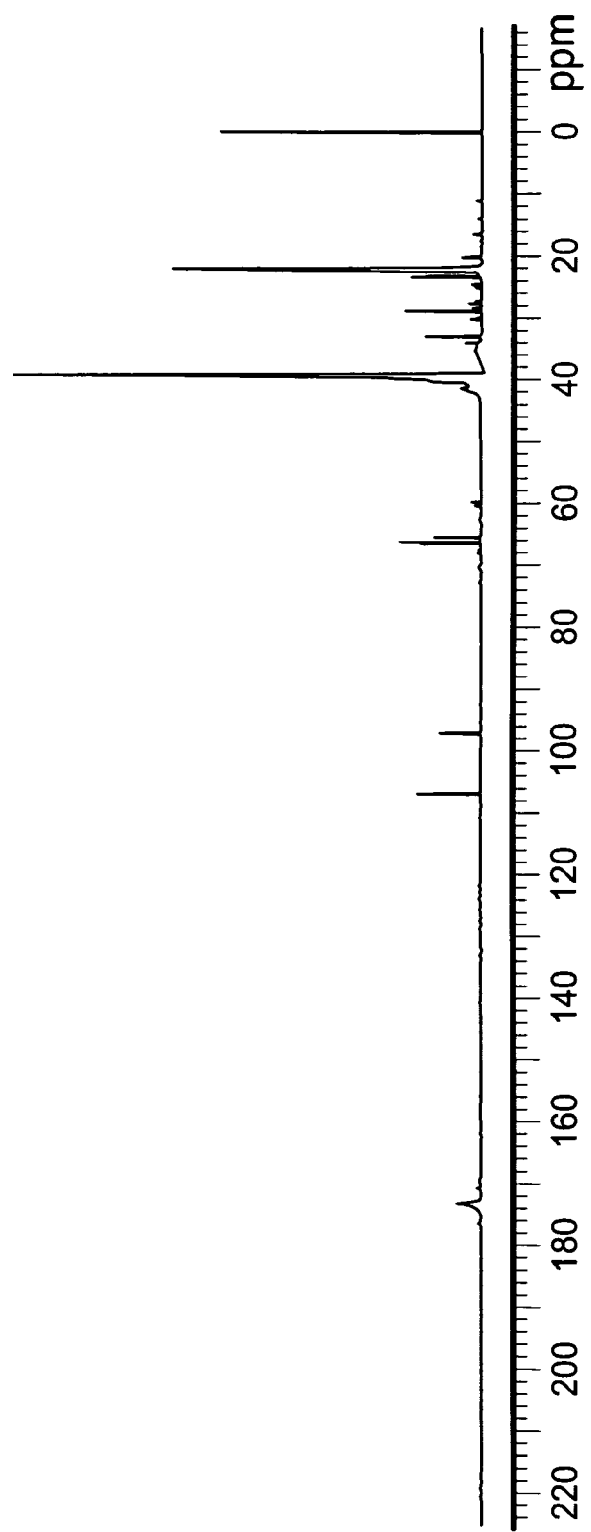
FIG. 7 shows a $^{13}$C NMR spectra (DMSO-$d_6$) of copolymers of poly(NIPAAm-co-HEMAPLA-co-AAc-co-HPG-MA), where the spectrum represents polymer sample HPG High.

[a]16.7 wt % in PBS, measured by DSC $^1$H NMR spectroscopy was used to confirm the incorporation of HPG macromer into the copolymer and is shown in FIG. 6. The obtained $^1$H NMR data verified that the polymer building blocks NIPAAm, HEMAPLA, AAc, and HPG-MA respectively) reacted at the intended molar feed ratios. FIG. 6 shows the stacked $^1$H NMR spectra for all the copolymers synthesized. FIG. 6 shows $^1$H NMR spectra (DMSO-$d_6$) of copolymers of poly(NIPAAm-co-HEMAPLA-co-AAc-co-HPG-MA), where the spectra represent (A) Control copolymer (no HPG); (B) HPG Low copolymer; (C) HPG Med copolymer; and (D) HPG High copolymer. Proton peaks characteristic of the monomer NIPAAm (methyl, 1.04 ppm) or macromers HEMAPLA (where the PLA component was observed at 5.1 ppm) and HPG-MA (methylene and methine, 3.4 ppm) were observed. A singlet peak is observed at δ=3.4 ppm in FIG. 6A arising from water in DMSO-$d_6$. This peak is shifted to ~3.3 ppm in FIGS. 6B-D, and in its place a small broad multiplet peak emerges at δ=3.4 ppm (CH, $CH_2$ protons of HPG). Furthermore, this broad peak occurring at 3.4 ppm grows in intensity (i.e., increased integral area) in going from spectra shown in FIG. 6B to 6D. Peaks corresponding to the polymerization solvent, 1,4-dioxane, also shift to this region, but as seen in FIG. 7 $^{13}$C NMR spectra for poly(NIPAAm-co-HEMAPLA-co-AAc-co-HPG-MA) where the spectrum represents polymer sample HPG High. The existence of AAc (—COOH) units and their relative amounts was approximated from the visible and integratable peak at 11.7 ppm. This approach was taken instead of the more common and accurate titration approach [28-29] because of the presence of hydroxyl groups on both the HPG and in the side chain acid groups of AAc.

$^{13}$C NMR spectra of the HPG High sample shown in FIG. 7 confirmed that little solvent remained as the corresponding peak at ~67 ppm was barely detected above the baseline noise (number of scans=10,000). Thus, in calculating the bulky HPG group into the polymer backbone via the approximately one acrylate group per HPG molecule. All of the copolymers have molecular weights between 1,200 and 3,700 g/mol and a polydispersity index of 1.5-1.7. Considering the fact that the GPC column was calibrated with linear polystyrene, the measured $M_n$ values for HPG high, HPG Med and HPG Low are expected to be problematic as the hyperbranched structure of the HPG component does not accurately correspond to the linear polystyrene calibrant. However, the GPC-determined molecular weight distribution of the copolymers can be used as a reference.

Figure 8:
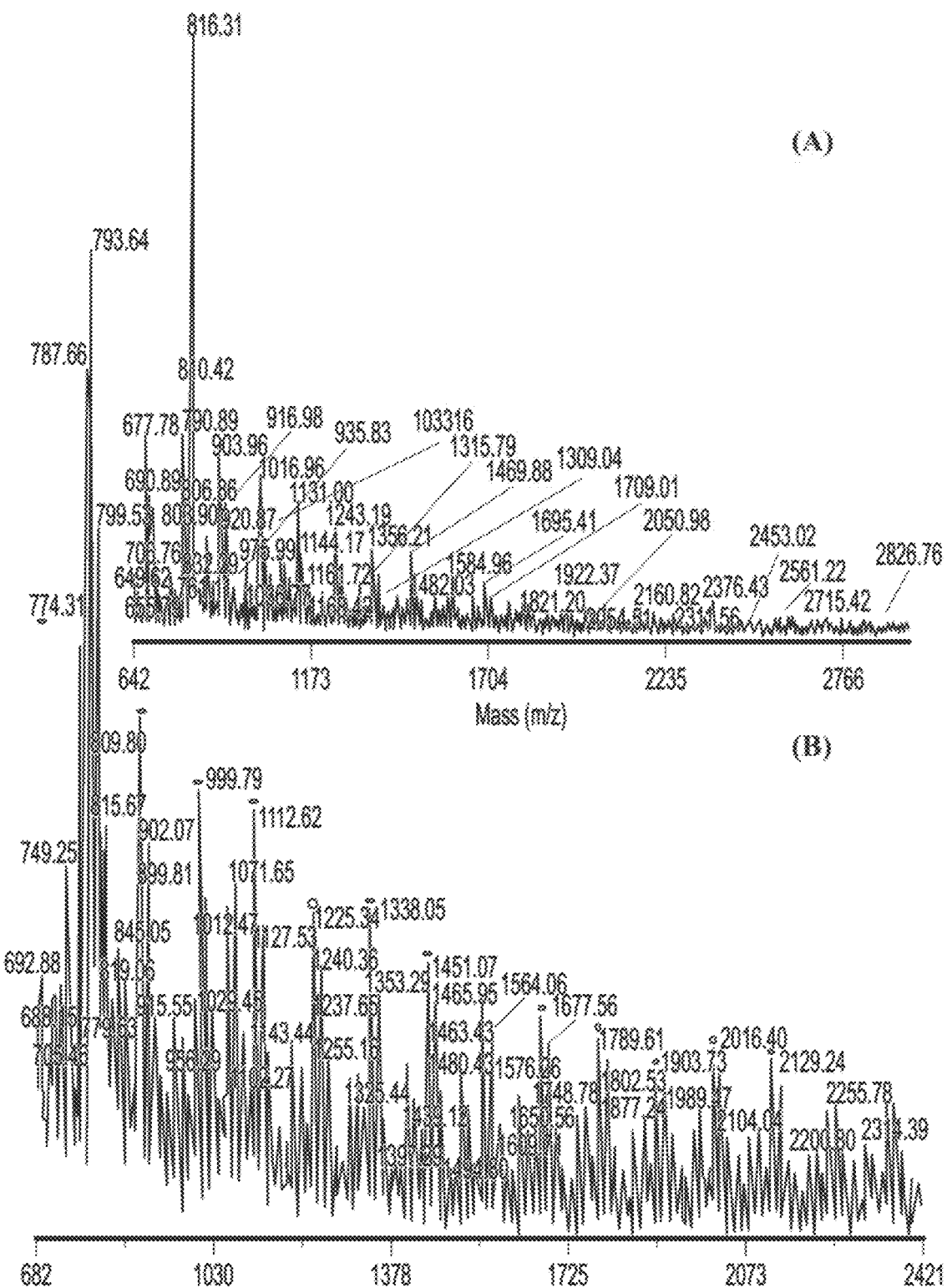
FIG. 8 shows MALDI of copolymers (A) HPG-High and (B) Control.

Further analysis of the molecular weight and its distribution for the HPG High and Control samples was obtained from MALDI MS. FIG. 8 shows the MALDI of copolymers (A) CONTROL and (B) HPG HIGH. HPG High was determined to have a number average molecular weight of 1,412 g/mole and a polydispersity index of 1.16. This value is 3 times lower than the value obtained by GPC. Others have observed hyperbranched polymers with up to 5 times lower molecular weights obtained by MALDI MS as compared to GPC [21]. The number average molecular weight $M_n$ calculated from the MALDI-TOF spectrum for Control is 1,164 g/mole which is in good agreement with the value of 1,253 obtained from GPC. FIG. 8 (A) shows the mass spectra of Control where the main peaks occur at m/z=678; 791; 904; 1,019; 1,131; 1,243; 1,357; 1,470; 1,583; 1,895; 1,809; 1,922. The mass difference (m/z=113) between these peaks precisely represents the molar mass of NIPAAm. Two additional subdistributions (starting with m/z=690.83 and 693.95) are also observed with a mass unit difference of 113 between peaks in the respective series. Evidence of AAc (MW=72) incorporation into the chains is provided by peaks occurring at m/z=716.63 and 788.63; 790.84 and 862.79; 1,171.45 and 1,243.16. In each of these three series, the mass difference exactly corresponds to 72. The mass difference between peaks occurring at m/z=1,243.16 and 1,372.64;

1,565 and 1,695.49; 1,738.77 and 1,869.05 precisely represents the molar mass of HEMA (m/z=130). In addition, a peak mass difference of 318 corresponding to HEMALac is also observed (m/z=716.63 and 1,035.05). No peaks were detected that corresponded to HPG in this control sample.

FIG. 8B shows the MALDI MS of sample HPG High. Starting with the peak at m/z=774.31, a series with mass difference corresponding to NIPAAm is observed (denoted by open circles above and to the left of peak mass numbers). A second series of peaks with mass unit difference of 130 is also observed in the spectra shifted to right of the first series by 15 mass units. Evidence of AAc incorporation into the chains is again observed. Peaks occurring at m/z=999.79 and 1,071.65; 1,325.44 and 1,397.29; 2,129.24 and 2,200.80 all represent exact mass unit difference of 72. A peak mass difference of 130 corresponding to HEMA (m/z=1,012.47 and 1,143.44) and 318 corresponding to HEMALac (m/z=809.8 and 1,127.53) were also observed. Incorporation of HPG-MA was confirmed by the peak mass difference of 142 detected in three areas of the spectra: m/z=774.31 and 916.31; 887.06 and 1,029.45; 1,338.05 and 1,480.43. One pair of peaks represented a mass difference of 74 (m/z=1, 802.53 and 1,877.24) which is exactly the mass for the monomer glycidol.

The LCST of Copolymers

Figure 9:
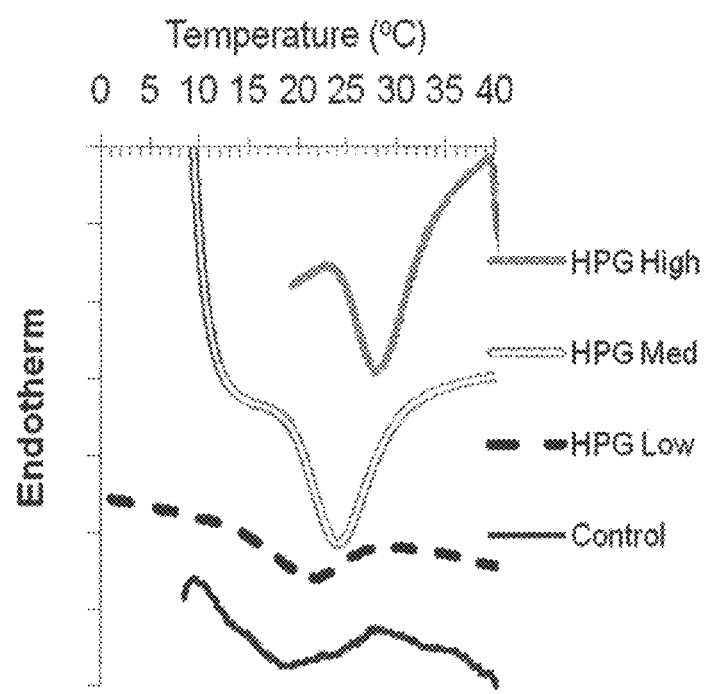
FIG. 9 shows LCST determination by DSC analysis for all solutions of poly(NIPAAm-co-HEMAPLA-co-AAc-co-HPG-MA): control, HPG low, HPG medium, and HPG high.

The LCST of the different copolymers was determined based on abrupt changes in optical and thermal properties of the materials. DSC measurements of thermogelling solutions is a common method used to describe the phase transition temperature [9, 13]. An endothermic peak occurs when a temperature is reached that induces hydrogen bond breaking in the water clusters around the hydrophobic domains and between the water molecules and amide bonds in the copolymers [30]. Typical DSC curves of copolymer solutions (16.7 wt % in PBS) showed broad but obvious endothermic peaks in the range of 20-28° C. as shown in FIG. 9. The gray box focuses on the temperature range where all transitions were observed as indicated by the minimum in the endotherm trace. The transition temperature shifts to lower values as the HPG content is reduced.

Figure 10:
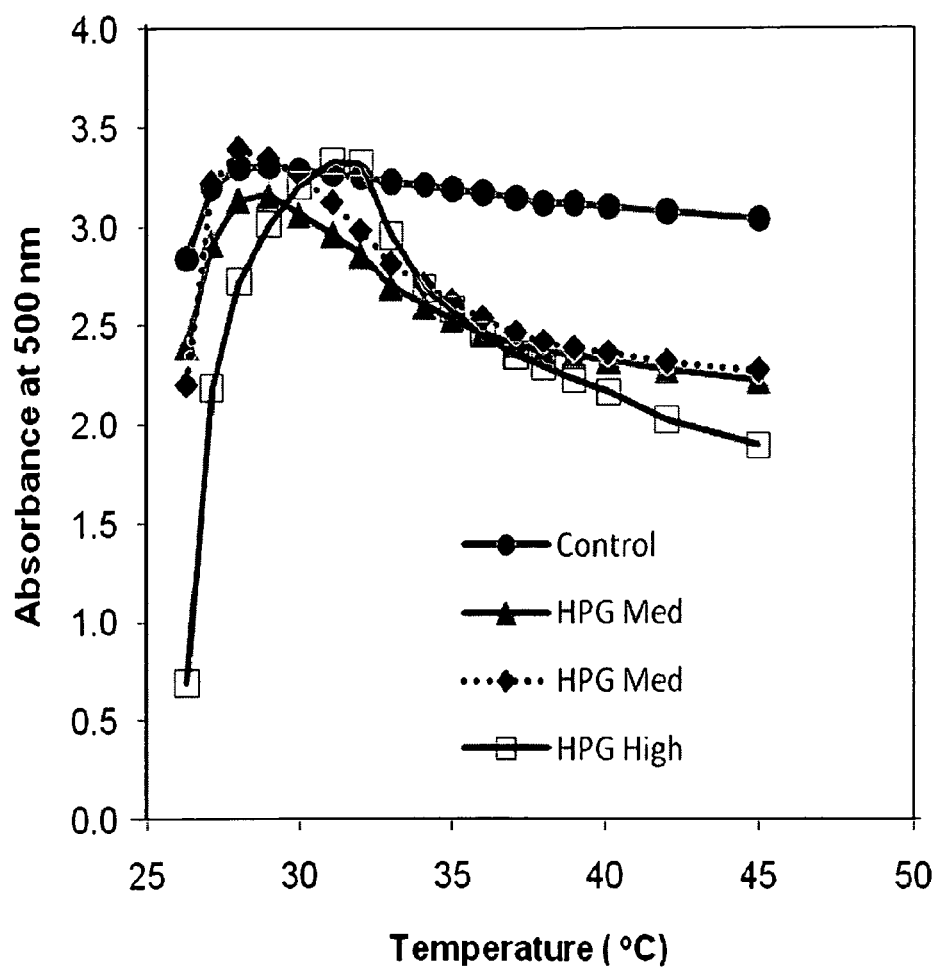
FIG. 10 shows LCST determination by measurement of copolymer solution optical absorption as a function of temperature.

A similar phenomenon was observed from optical absorption data, where a jump in absorption is observed at a certain temperature. FIG. 10 shows LCST determination by measurement of copolymer solution optical absorption as a function of temperature.

Although light scattering studies of the copolymer solutions were not performed, others have observed a similar jump in optical absorption and attributed this to micelle formation at a certain temperature [13]. It should be noted that the transitions observed for the copolymers presented here are very close to room temperature and the instrument capabilities were limited to 25-45° C. Therefore, the ramp up in the optical absorption was not observed over the entire critical range for all the copolymers. Instead, the peak maximum was the only observable part of the transition range for all but the HPG High sample.

Cytotoxicity

Figure 11:
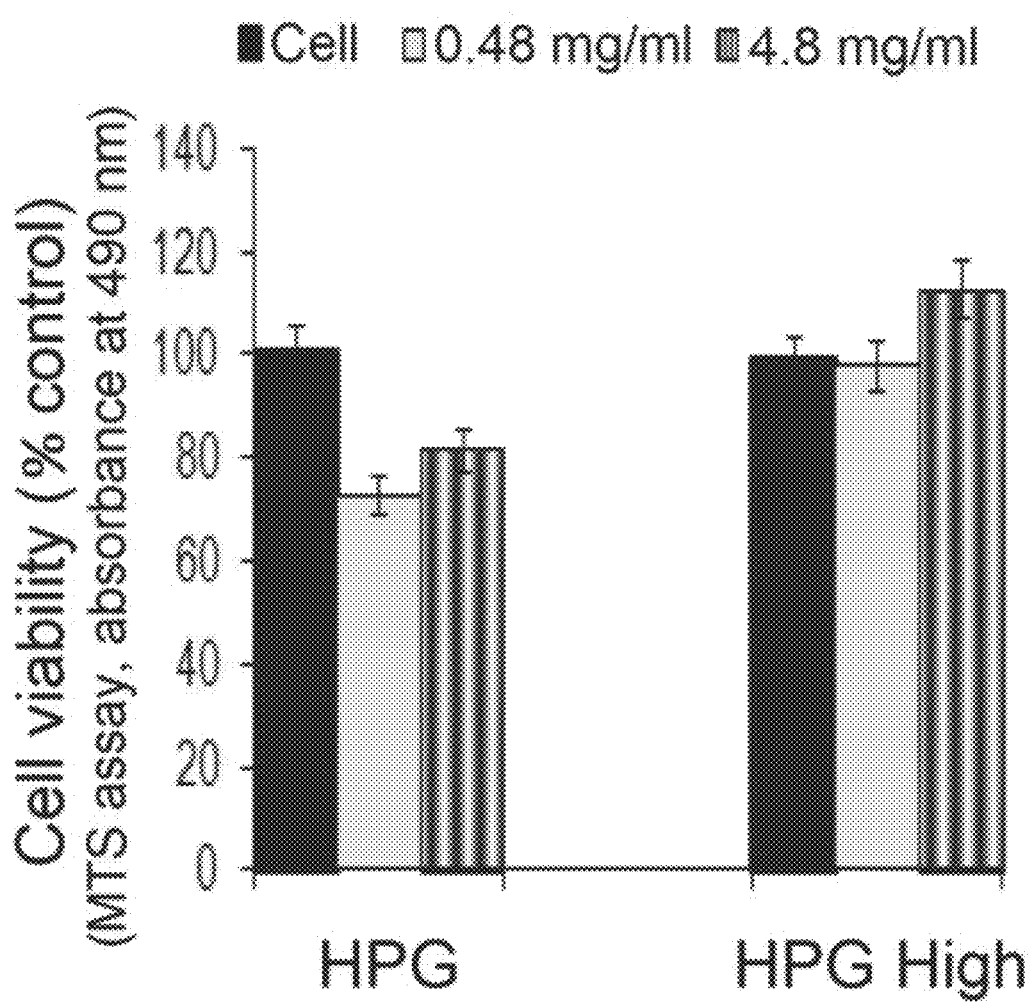
FIG. 11 shows results of MTS assay to measure the cytotoxicity of HPG or copolymer HPG High at various concentrations.

Uterine fibroid cells grown to 80% confluency show no negative effects on viability and metabolic activity after exposure for 72 h to medium containing either HPG or copolymer HPG High. FIG. 11 shows the results of a MTS assay to measure the cytotoxicity of HPG or copolymer HPG High at various concentrations. The materials were incubated with cultured fibroid cells for a total of 72 h before assessing cell viability in each group (n=2). No statistically significant difference was noted relative to the control. This finding is promising for the potential application of the copolymer hydrogels as a localized drug delivery system for treatment of uterine fibroids.

Degradation Studies

HPG High was characterized by GPC to determine modality and efficiency of the polymerization reaction [31] as well as the copolymer's degradation by a loss of molecular weight. FIG. 12 shows Degradation studies of 16.7 wt % copolymer gel HPG High at 37° C. showing GPC curves FIG. 12A and change in the molecular weight with time FIG. 12B.

The GPC chromatograms for HPG High lypholized samples became monomodal over successive days of degradation (FIG. 12A) and shifted towards lower molecular weights as degradation time increased. This result is consistent with GPC curves for homopolymers of PLA (158.5 kg/mol) reported by Weir et al to remain monomodal throughout successive weeks of degradation [32]. It should be noted that lyophilized samples of HPG High obtained after 6 days of incubation presented THF insoluble fractions even after stirring in THF for several hours. Presumably, the insoluble fractions represent the HPG component of the copolymer as HPG macromer is insoluble in THF. Thus, it is expected that the GPC traces should narrow in polydispersity as PLA chains are hydrolytically cleaved. In fact, the GPC chromatogram did show a decrease in polydispersity index (PDI) from 1.7 to 1.3 after complete hydrolysis. Before hydrolysis, the polydispersity is affected by both the composition and degree of polymerization. After hydrolysis, the affect of the composition on the polydispersity is reduced and the degree of polymerization becomes the main determinate of the polydispersity. FIG. 12B presents the GPC-generated findings that show a relatively fast decrease in molecular weight over a six day period. Hydrolysis of the PLA containing chains leads to mass loss. Within the first 16.5 hours, the copolymer has lost 95% of its PLA molecular weight. These findings are consistent with reported PLA degradation kinetics which range from days to weeks based on crystallinity, molecular weight and distribution, orientation, unreacted monomer, and the presence of impurities [33]. In addition, although the GPC curve of HPG High before hydrolysis (Day 0, shown in FIG. 12(A)) is broad, lower molecular weight impurities, unreacted starting materials, side products, and so forth, were not detected demonstrating the efficiency of the polymerization.

Figure 13:
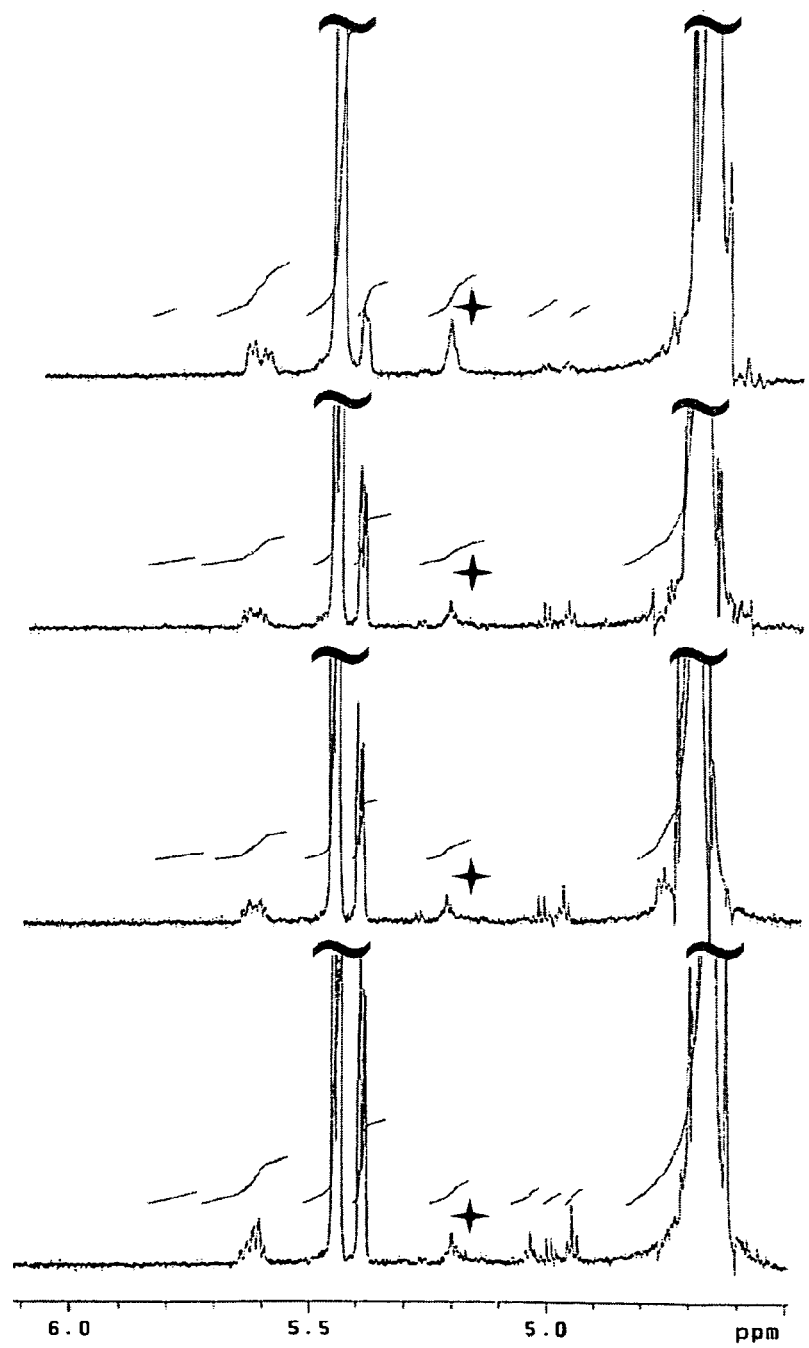
FIG. 13 shows $^1$H NMR data showing spectral changes during the hydrolytic degradation of a representative poly (NIPAAm-co-HEMAPLA-co-AAc-co-HPG-MA) sample.

FIG. 13 shows $^1$H-NMR ($D_2O$) spectral change during hydrolytic degradation of a representative poly(NIPAAm-co-HEMAPLA-co-AAc-co-HPG-MA) sample: (A) after 0 hours; (B) 15 hours; (C) 21 hours; and (D) 56 hours of degradation. In this figure, the HEMA-lactate peak (methane proton, 1 H) at 5.2 ppm disappeared as the ester linkages of the polylactic acid spacers hydrolyzed during incubation. After 15 hours, there is a sharp decrease in the peak and after 21 hours in the peak is no longer amendable to integration. These results are consistent with the finding reported from GPC analysis of the degradation product. This degradation trend is in agreement with the previous report on copolymers based on NIPAAm, HEMAPLA, and AAc; [34] Copolymer design alterations aimed at slowing the degradation rate would be concomitant with impacts on other copolymer properties such as the LCST.

The system allows a wide variety of diagnostic and therapeutic molecules for local delivery to target tissues without the need for modification of the drug, or therapeutic agent. The liquogel including a drug or active agent is mixed with an aqueous solvent before being used. Nonlimiting examples of solvents are water, saline and phosphate buffered saline.

The HPG nanocarrier may be injected into the treatment site. Local injection under imaging guidance would allow for exact tissue placement of the drug or therapeutic agent. Drugs or therapeutic agents that can be used to treat a disease or disorder can be used. For example, local delivery of hormones or other antiproliferative and antifibrotic drugs directly to a fibroid has the potential to decrease fibroid growth and size without systemic side effects. For treatment of uterine fibroids the HPG nanocarrier may be injected into the fibroid through the abdomen or intravaginally. The HPG nanocarrier can be injected into a tumor in the breast or other location.

The type of drug or therapeutic agent that can be used in the delivery system is one that suitable for treatment of the particular disease or condition.

In an aspect of the invention, the therapeutic agent that can be used to prevent or treat uterine fibroids is selected from anti-fibrotic agents such as a Transforming Growth Factor beta (TGFβ) inhibitors. TGFβ inhibitors that can be used include P144, a fourteen amino acid long peptide that inactivates TGFβ and has been shown to reduce soluble collagen content in skin fibrosis 2) SB-525334, a small molecule TGFβ inhibitor with a polyaromatic-ring-structure shown to reduce fibroids in a rat model and CDB-4124, a selective progesterone receptor modulator (SPRM) thought to inhibit cell proliferation and fibrosis can also be used as the active agent.

Other types of drugs that can be used are Tamoxifen, letrozole, anastrozole, exemestane, trastuzumab, doxorubicin, cyclophosphamide, paclitaxel, docetaxel, fulvestrant and camptothecin.

Figure 14:
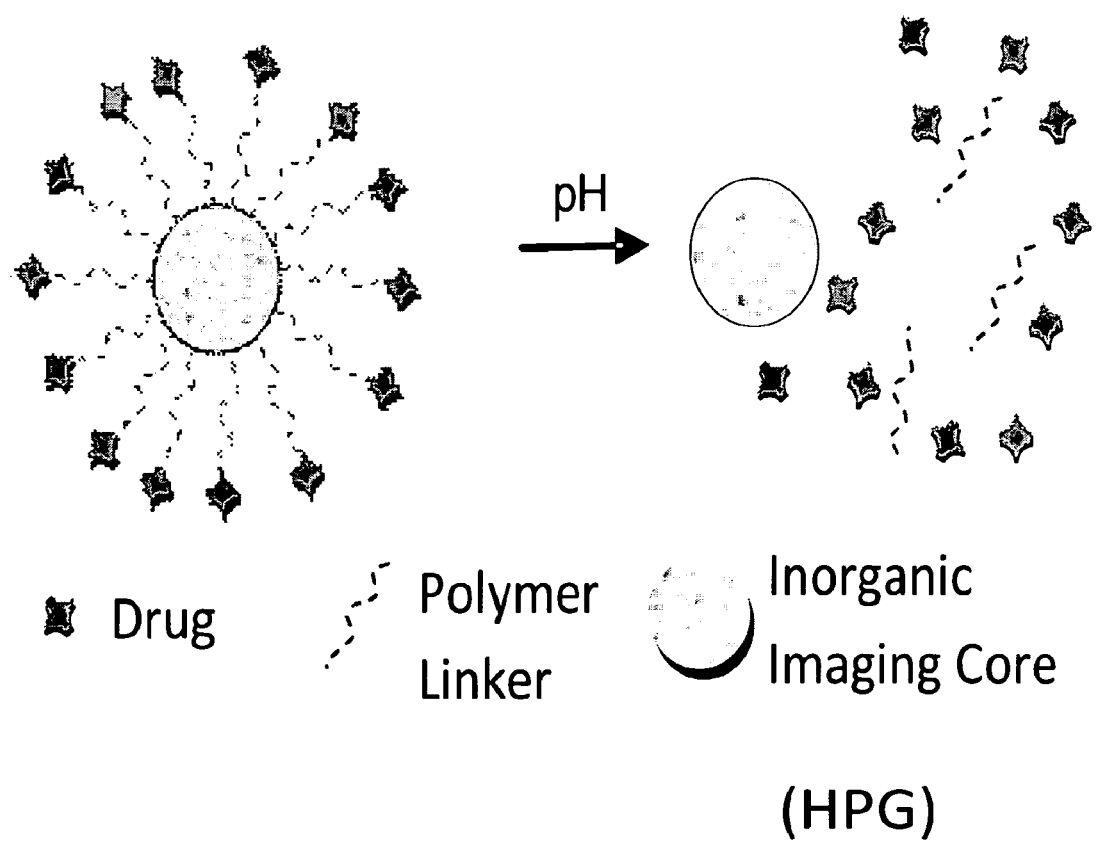
FIG. 14 shows a delivery system with a pH responsive component.

Another aspect of the invention is a delivery system that releases the drug or therapeutic agent by an external pH trigger. This can facilitate tracking of the drug biodistribution. FIG. 14 illustrates a drug delivery system triggered to release drug in response to pH changes. The system consists of: (1) HPG (core circle); (2) a pH responsive polymer link (black wavey line); and (3) a covalently attached drug. Non limiting examples of pH responsive polymer linkers derived from hydrazones, (37) orthoesters, (38) and acetals, (39-43) that are pH-sensitive (44). These linkers are protonated within the endosome (pH ~5.5-6) as protons are pumped over the endosome's plasma membrane but not out of the endosome (pH 7.4). Repulsions between charges contribute to endosomal swelling. The accumulation of positive charge in the endosome causes the influx of chlorine ions and water until the endosome ruptures, releasing the drug or therapeutic agent into the cytosol.

Figure 15:
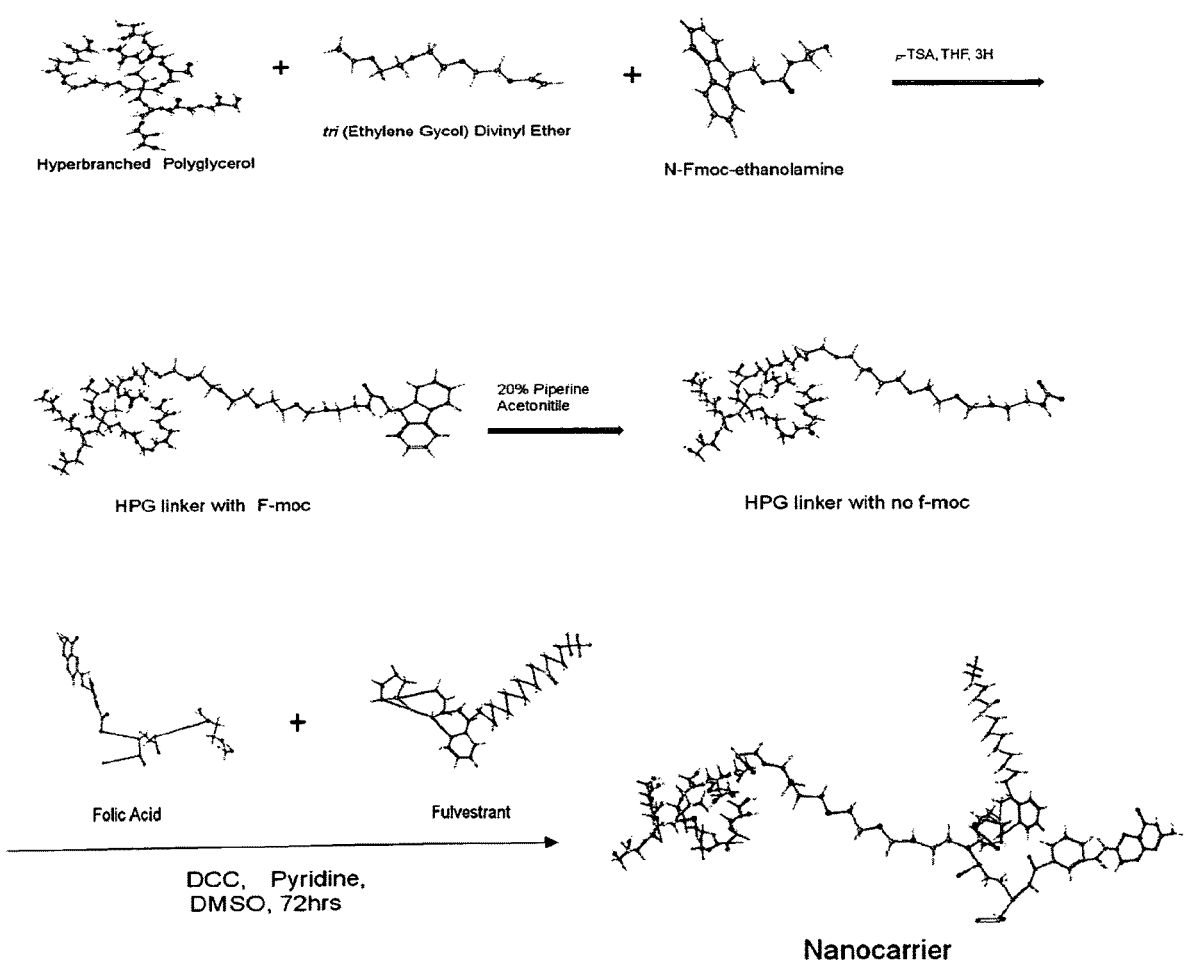
FIG. 15 schematic of synthesis to prepare HPG based drug delivery system with pH sensitive linkers.

A non-limiting aspect of this invention is a polymeric carrier involving hyper branched polyglycerol (HPG)/tri (ethylene glycol) divinyl ether/drug. A synthesis is shown in FIG. 15 which shows a synthesis to prepare HPG based drug delivery systems with pH sensitive linkers. HPG is combined with tri(ethylene glycol) divinyl ether and Fmoc-ethanolamine. Fmoc is cleaved to produce the unprotected terminal acid groups of the nanocarrier and of folic acid (squares) and fulvestrant drug (ovals) are covalently linked to nanocarrier.

A further description of a method for preparing the bifunctional pH-sensitive polymeric drug delivery system is described Experimental Design: HPG and tri(ethylene glycol) divinyl ether were copolymerized with Fmoc-serinol in anhydrous tetrahydrofuran (THF) (70% yield). The protecting group was removed in piperidine (55% yield) prior to forming a covalent conjugate between the HPG-linker macromer, folic acid, and fulvestrant. The latter reaction was followed by TLC over the course of three days to monitor extent of coupling. $^1$H NMR was performed on a 400 MHz in deuterated chloroform.

Another preparation could involve the following: a solution of the drug in anhydrous tetrahydrofuran (THF) added to a rigorously dried mixture of HPG and p-toluenesulfonic acid monohydrate (p-TSA) followed by a solution of tri (ethylene glycol) divinyl ether in anhydrous THF. Triethylamine will be added to complex the p-TSA catalyst and the mixture will be precipitated from hexane.

Other methods known to those in the art can be used to prepare this delivery system.

Results: $^1$H NMR confirmed the synthesis of HPG-linker copolymerized with Fmoc-serinol. Characteristic peaks were observed at 1.32-2.31 ppm (acetal groups), 3.16 and 3.50-3.82 ppm (HPG), 5.00-5.10 ppm (acetal groups between the HPG-Linker), and 7.26-7.73 ppm (aromatic rings on Fmoc). Deprotection of the Fmoc was confirmed by the absence of characteristic peaks at 7.3-7.6 ppm while the doublets at 7.1 and 7.7 ppm remained confirming the presence of amine groups. The attachment of folic acid and fulvestrant were followed by TLC showing an elongated new peak ($R_f$=0.4) after 18 hours. See FIGS. 21 to 25.

This bifunctional pH-sensitive polymeric drug delivery system can also be used for local delivery of a drug or therapeutic agent. For example this delivery system can be used to treat breast cancer. The covalently attached folic acid will enhance the tumor targeting properties of the delivery system while increasing the solubility of fulvestrant and the feasibility of delivering this anti-cancer drug with a high payload. The nanocarrier can target estrogen receptors with high affinity, by covalently linking folic acid, while releasing the native form of fulvestrant with full activity in response pH.

The one or more drugs or therapeutic agents are entrapped or attached into the liquogel or polymeric delivery system by a method known to those of skill in the art. In most cases, the drug or active agent(s) are non-covalently or hydrogen bonded to the liquogel.

The preparations normally contain about 1 to 99%, for example, about 5 to 70%, or from about 5 to about 30% by weight of an active ingredient.

The liquogels with the active compounds are administered at a therapeutically effective dosage sufficient to prevent or treat the disease or condition. The liquogels may be administered in single or multiple doses. Physiologically acceptable carriers can be used with liquogels, nanocarriers and pH polymeric delivery systems.

The dose of drug or therapeutic agent to be administered is selected to suit the desired effect. Actual dosage levels of the drug or therapeutic agent in the compositions of this invention may be varied so as to obtain an amount of the drug or agent, which is effective to achieve the desired therapeutic response for a particular patient, without causing undue side effects or being toxic to the patient. The dose may be determined by the time of administration, the rate of excretion of the particular compound being employed, the duration of the treatment, other drugs, compounds and/or materials used in combination with the particular compounds employed, the age, weight, condition, general health and prior medical history of the patient being treated, and like factors well known in the medical arts.

It should be noted that, as used in this specification and the appended claims, the singular forms "a," "an," and "the"

include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

In this application, the use of the singular includes the plural and plural encompasses singular, unless specifically stated otherwise. In addition, in this application, the use of "or" means "and/or" unless specifically stated otherwise, even though "and/or" may be explicitly used in certain instances.

Also as used herein, "and/or" refers to and encompasses any and all possible combinations of one or more of the associated listed items, as well as the lack of combinations when interpreted in the alternative ("or").

For purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the are approximations that may vary depending upon the desired properties to be obtained by the present invention. Any numerical value, however, inherently contains certain errors necessarily resulting from the standard variation found in their respective testing measurements.

The invention has been described with reference to various specific and preferred embodiments and techniques.

The invention is further understood by reference to the following Examples, which are intended to be purely exemplary of the invention. The present invention is not limited in scope by the exemplified embodiments, which are intended as illustrations of single aspects of the invention only. Any methods that are functionally equivalent to those described in the Examples are within the spirit and scope of the invention.

EXAMPLES

Example 1

HPG (Mn,MALDI=1096 g Mw/Mn=1.13) was prepared according to the literature by controlled anionic polymerization of glycidol [21], The average number of terminal hydroxyl groups per HPG molecule was approximately 29 as determined by the relative integrals from the inverse gated $^{13}$C NMR spectra. (FIG. 21) Glycidyl methacrylate (GMA), Acrylic acid (AAc), and N-isopropylacrylamide (NIPAAm) were purchased from Sigma-Aldrich (St. Louis, MO). AAc was purified immediately prior to use by passage through a basic alumina column. NIPAAm was recrystallized from hexane and vacuum dried. Benzoyl peroxide (BPO), stannous 2-ethylhexanoate [(Sn(Oct)$_2$],(3S)-cis-3,6 Dimethyl-1,4-dioxane,-2,5 dione (98%) (L-lactide), 4-(N,N-diethylamino)pyridine (DMAP), anhydrous dimethyl sulfoxide (DMSO), anhydrous 1,4-dioxane, methyl sulfoxide-d6 (99.9% atom D), anhydrous methanol, tetrahydrofuran (THF), and phosphate-buffered saline (PBS) were purchased from Fisher Scientific (Pittsburgh, PA). All polymerizations were carried out under a dry nitrogen atmosphere.

Synthesis

Synthesis of HPG-MA. Methacrylated HPG was synthesized essentially as described by Oudshoorn et al. [26]. As shown in FIG. 1, HPG-MA structures were prepared by functionalization of the HPG hydroxyl groups with glycidyl methacrylate.

Synthesis of HEMAPLA. HEMAPLA was synthesized by ring-opening polymerization of L-lactide initiated by HEMA with Sn(Oct)$_2$ as a catalyst (FIG. 1). Equivalent molar ratios of HEMA and lactide were reacted at 110° C. in a nitrogen atmosphere for 1 h in the presence of catalyst Sn(Oct)$_2$ (121.5 mg, 1 mol % with respect to HEMA). The cooled reaction mixture was dissolved in THF and precipitated in ice cold water. The precipitate was dissolved in ethyl acetate and filtered to remove the remaining solids. The filtrate was dried over MgSO$_4$ and concentrated under reduced pressure to obtain purified HEMAPLA.

Synthesis of Poly(NIPAAm-co-HEMAPLA-co-AAc-co-HPG-MA). Poly(NIPAAm-co-HEMAPLA-co-AAc-co-HPG-MA) copolymers were synthesized by free radical polymerization (FIG. 1). All glassware was dried at 120° C. for 12 h and flamed in a vacuum to eliminate moisture before use. A 5 wt % solution of monomers (NIPAAm and AAc) and macromers (HEMAPLA and HPG-MA) in 1,4-dioxane was introduced in a dry, preweighted round-bottom flask equipped with rubber septum and a magnetic stir bar. A solution of BPO ($7.2 \times 10^{-3}$ mol/mol monomer) in 1,4-dioxane was added. The polymerization was conducted at 70° C. for 24 h under nitrogen atmosphere. The copolymer was purified by precipitation in hexane followed by precipitation from THF into diethyl ether and vacuum dried.

Characterization

Nuclear Magnetic Resonance. $^1$H and $^{13}$C NMR spectra were recorded in deuterated dimethyl sulfoxide (unless otherwise noted) on a Varian spectrometer operating at 500 MHz. Chemical shifts (δ) are reported in parts per million (ppm) downfield relative to tetramethylsilane (TMS 0.0 ppm ($^1$H) and 77.0 ppm ($^{13}$C).

Matrix-Assisted Laser Desorption and Ionization Time-of-Flight Mass Spectrometry (MALDI-TOF-MS). An Applied Biosystems Voyager-DE PROmass spectrometer equipped with a nitrogen laser (337 nm) was used to collect mass spectra data. A 32 ns delay was applied before ions were accelerated to 25 kV and positive ions detected. Additionally, the grid and guide wire voltages were set at 90% and 0.15% of the applied acceleration voltage, respectively, to focus the beam of ions. Typically, 40 laser shots were averaged for each spectrum. 4'-hydroxyazobenzene-2-carboxylicacid (HABA) was used as the matrix. The 1-100 mM matrix and analyte stock solutions were prepared as methanol solutions and were mixed in microcentrifuge tubes at matrix/analyte ratios varying from 1:1 to 1000:1; 1-2 δµl of this solution was applied to the sample plate and air-dried.

Electrospray Ionization Time-of-Flight Mass Spectrometry (ESI-TOF MS). ESI-TOF mass spectrometry was performed using a Micromass Q-tof micro (Waters Corp., Milford, MA). Samples were dissolved in methanol (0.1 or 1 mg mL$^{-1}$, HPG or HPG-MA, respectively) and passed (0.5-1) µL min$^{-1}$) through a nano-ESI source operated in positive ion mode with a capillary voltage of 2-3 kV, sample cone voltage of 33 V, source temperature of 90° C. and desolvation temperature set at 180° C. Nitrogen was used as the nebulizing gas. Sodium iodide cesium iodide was used to calibrate masses from m/z 400 to 1990 Da. Data was collected in continuum mode for 3-10 min over the same mass range with a 1 s scan time and 0.1 s inter scan time. Spectra were collected and processed using Masslynx 4.0 software (Waters).

Gel Permeation Chromatography (GPC). The molecular weights and molecular weight distributions of synthesized copolymers were determined by GPC unless otherwise noted. A Waters Alliance System, Waters 2695 Separations Module and Waters 2414 Refractive Index Detector (Waters Associates Inc., Milford, MA) were utilized. Approximately 20-30 mg of copolymer was dissolved in THF and the GPC analysis was performed at 35° C. The flow rate was 1.0 ml/min. A polystyrene standard kit was used for molecular weight elution volume calibration.

Differential Scanning calorimetry (DSC). Measurements were carried out on a Perkin-Elmer Pyris 1 DSC equipped with a cyrofill liquid nitrogen cooling system. LCSTs of the copolymer solutions in PBS (16.7 wt %) were studied using a scanning rate of 5° C./min over a temperature range of −10 to 45° C. The temperature at the maximum of the endothermal peak was recorded as the LCST [27].

UV-Vis. LCSTs of the copolymer solutions in PBS (16.7 wt %) were studied by measuring optical absorption. A SpectraMax M5e Microplate Reader (Molecular Devices, Inc., Sunnyvale, CA) was operated in single wavelength mode at 500 nm over a temperature range of 25 to 45° C. The LCST of each copolymer was determined in triplicate.

In vitro degradation. The cold copolymer solutions in PBS (16.7 wt %) were poured into 2 mL vials and incubated for different periods of time at 37° C. At predetermined times, samples were quenched in liquid nitrogen and frozen until needed for further studies. The frozen samples were lyophilized and the molecular weights of the copolymers were determined by GPC.

Cytotoxicity Assay

Sterile phenol red free Dulbecco's modified Eagle's medium (DMEM-F12) was purchased from Lonza (Walkersville, MD). FBS (fetal bovine serum) and antibiotics were obtained from Sigma.

Human uterine fibroid tissue was obtained from the existing IRB approved infrastructure of the Uterine Fibroid Tissue Repository which is part of Duke University School of Medicine Research Foundation's tissue banking operation. The fibroid cells were isolated by enzymatic digestion of fibroid tissue obtained at hysterectomy and cultured in DMEM-F12 medium supplemented with antibiotics, antimycotic and 10% FBS. In general, third passage cells were used in the cytotoxicity studies. Polymer solutions (16.5 wt % in PBS) were filtered through 0.22 μm filters (VWR 28145-501 polyethersulfone sterile filters). Cells were plated in 24-well plates and incubated for 24-48 h until 80% confluent. Then, cells were washed with prewarmed PBS and incubated with fresh media and HPG containing copolymer hydrogel or HPG macromer (0.09-90 μg/mL) for 72 h. Each concentration was measured four times.

Cytotoxicity was assessed with a methyl tetrazolium salt (MTS) assay kit (Promega, CellTiter96® AQueous Non-Radioactive Cell Proliferation Assay) following the protocol provided by the manufacturer and a 3 h incubation time. Results are expressed as percent viability relative to control cells grown in media alone (100% viability). The assay was repeated with fibroid cells from a different patient. Microscopy was used to help verify assay results.

Example 2

Figure 18:
FIG. 18 illustrates the transition from a clear solution to a gel.
Figure 18:
Figure 18:

The thermoresponsive nature of a liquogel according to the invention in 16.5 wt % phosphate buffered saline (PBS) solution was investigated to determine the lower critical solubility temperature (LCST) at which gelling begins to occur. The solution that is clear at 10° C. progresses to cloudy at 24° C. to a solid gel at 35° C. These results are shown in Table 2 and FIG. 18.

TABLE 2

Qualitative observation of the liquogel gelation temperature

| Temperature (° C.) | Visual Appearance |
|---|---|
| 0 | Clear |
| 24 | Cloudy |
| 28 | Solid firming |
| 30 | More liquid + solid |
| 35 | Gels |

Figure 19:
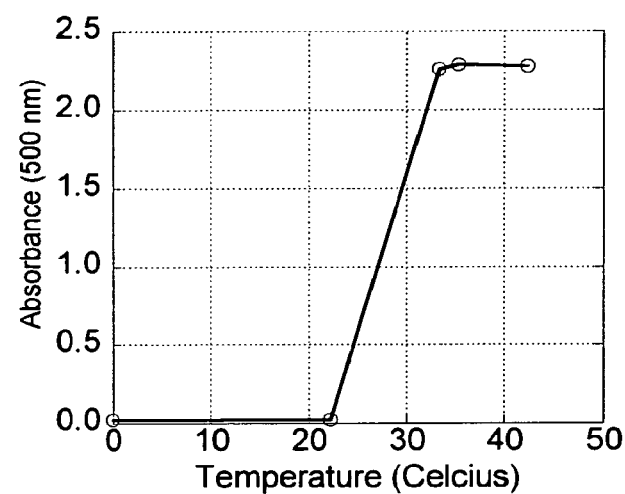
FIG. 19 shows optical absorption of the liquogel as a function of the temperature observation of the liquogel transition temperature.
Figure 20:
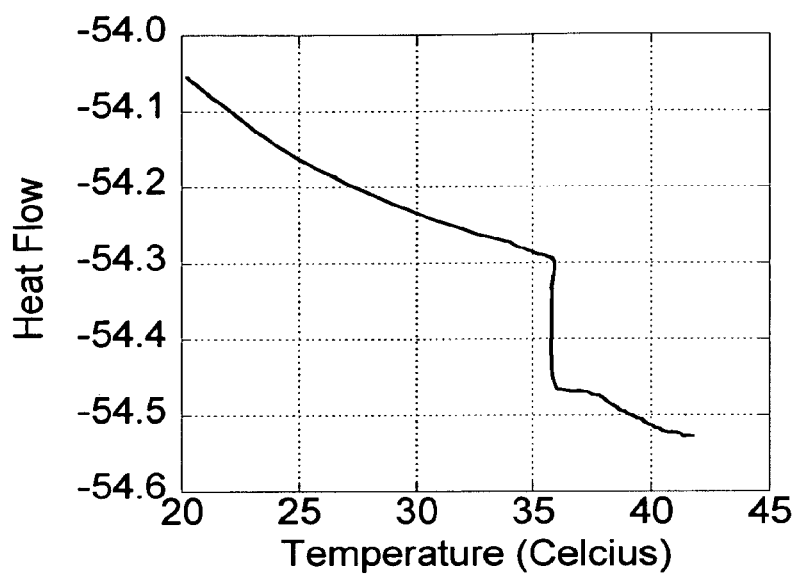
FIG. 20 shows a differential scanning calorimetry (DSC) curve showing transition in liquogel at 35.7° C., heating rate, 10° C./min.
Figure 21:
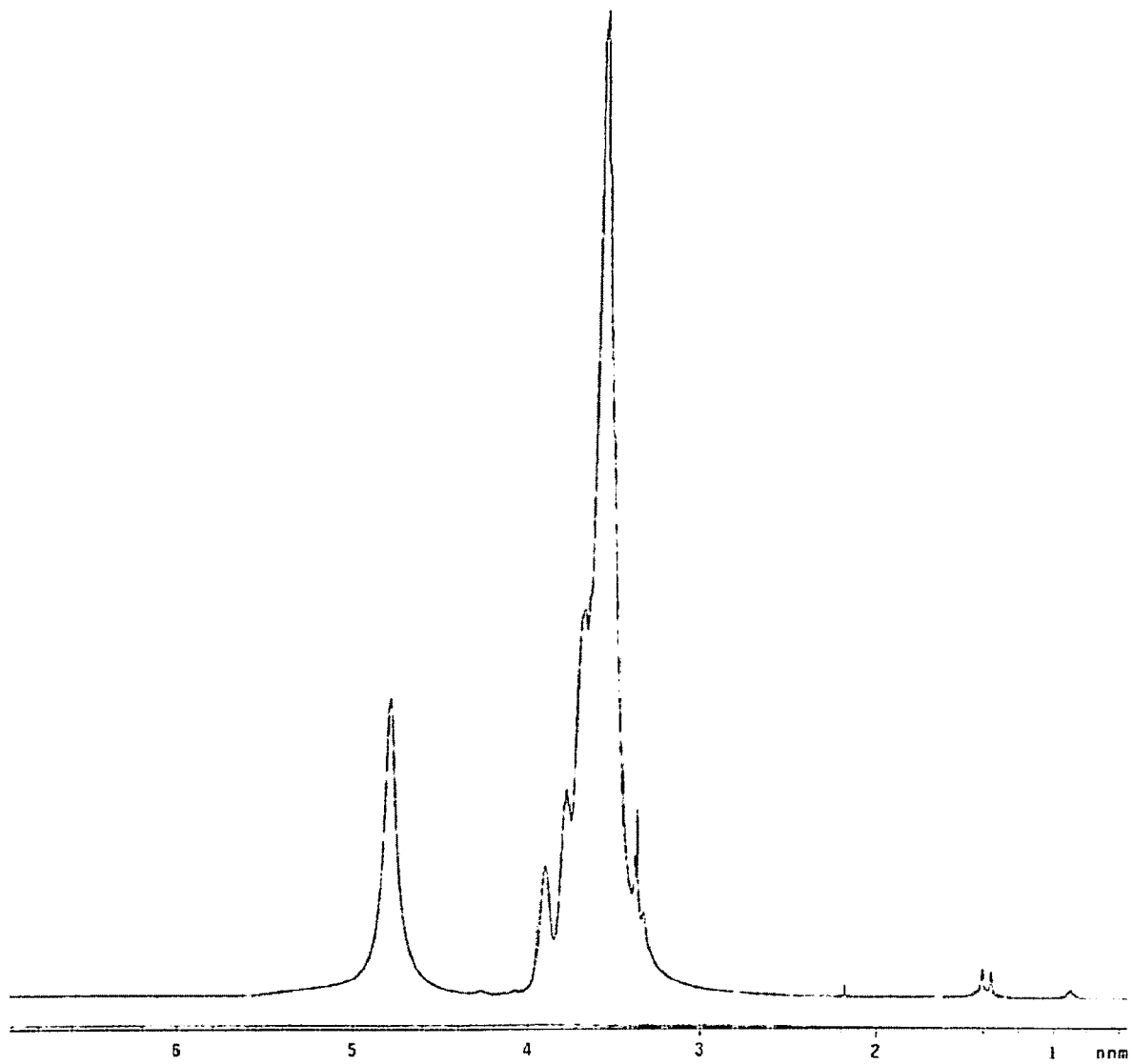
FIG. 21 shows $^1$H NMR spectra (CD3OD) of hyperbranched polyglycerol (HPG) obtained from anionic polymerization initiated with 1,1,1-tris(hydroxymethyl)propane.
Figure 22:
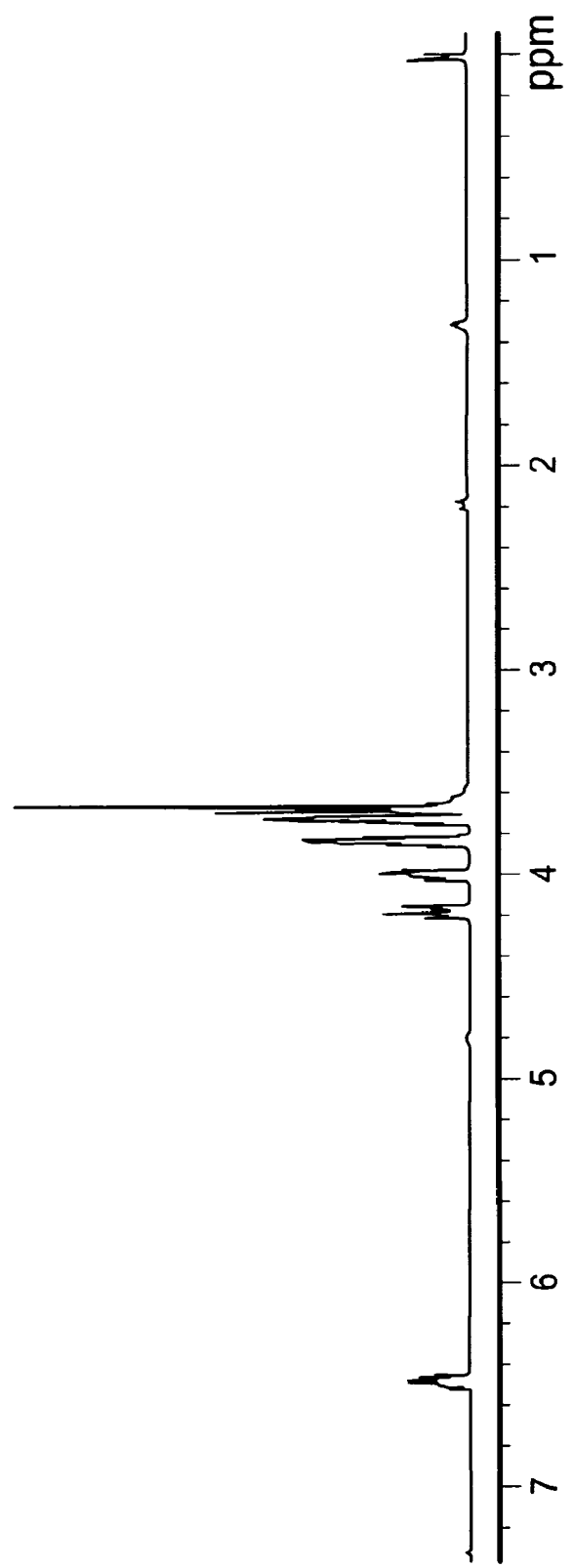
FIG. 22 shows $^1$H NMR ($S_H$, 500 MHz, CDCL3): of TEGDVE linker.
Figure 23:
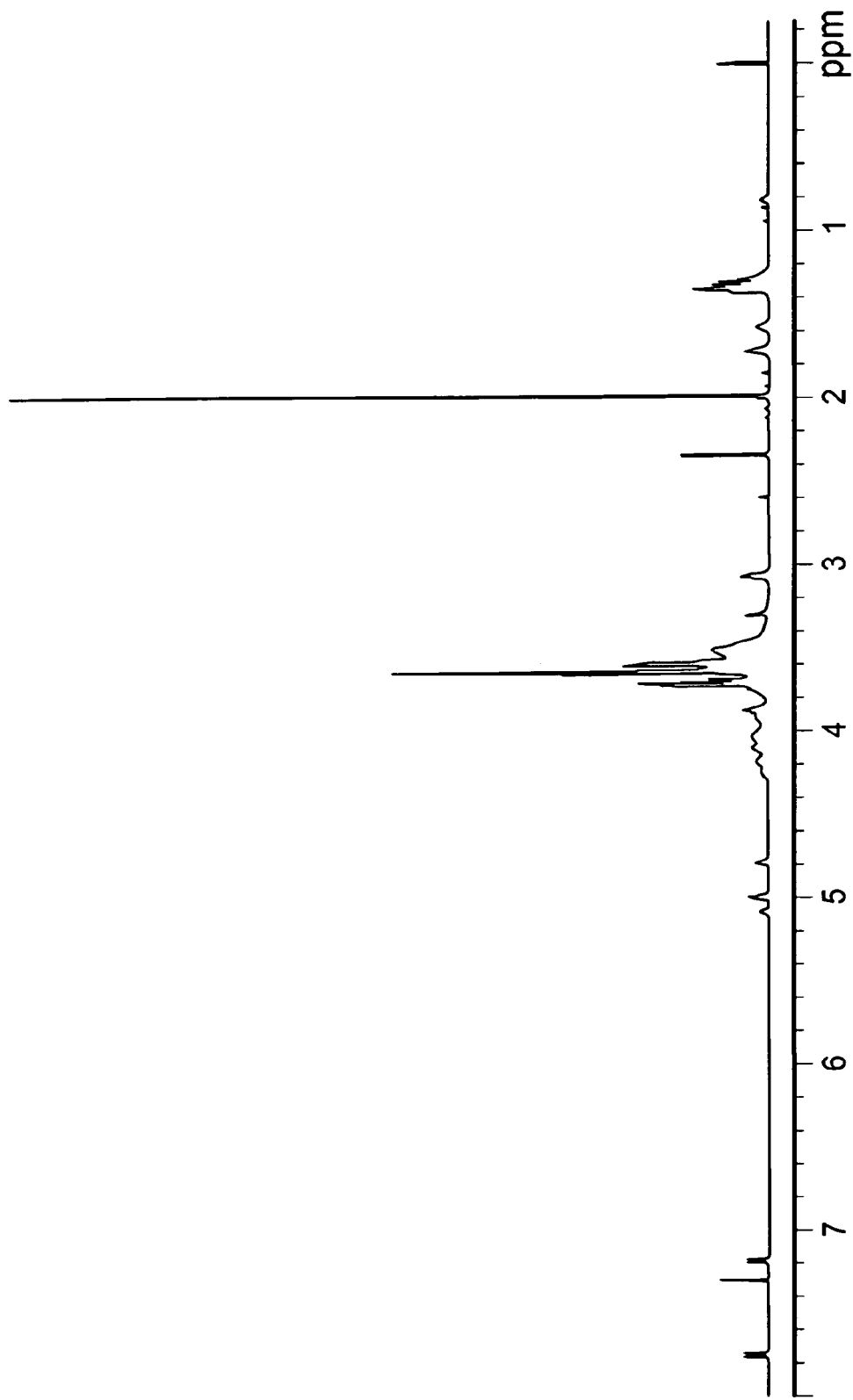
FIG. 23 shows $^1$H NMR of HPG-linker conjugate.
Figure 24:
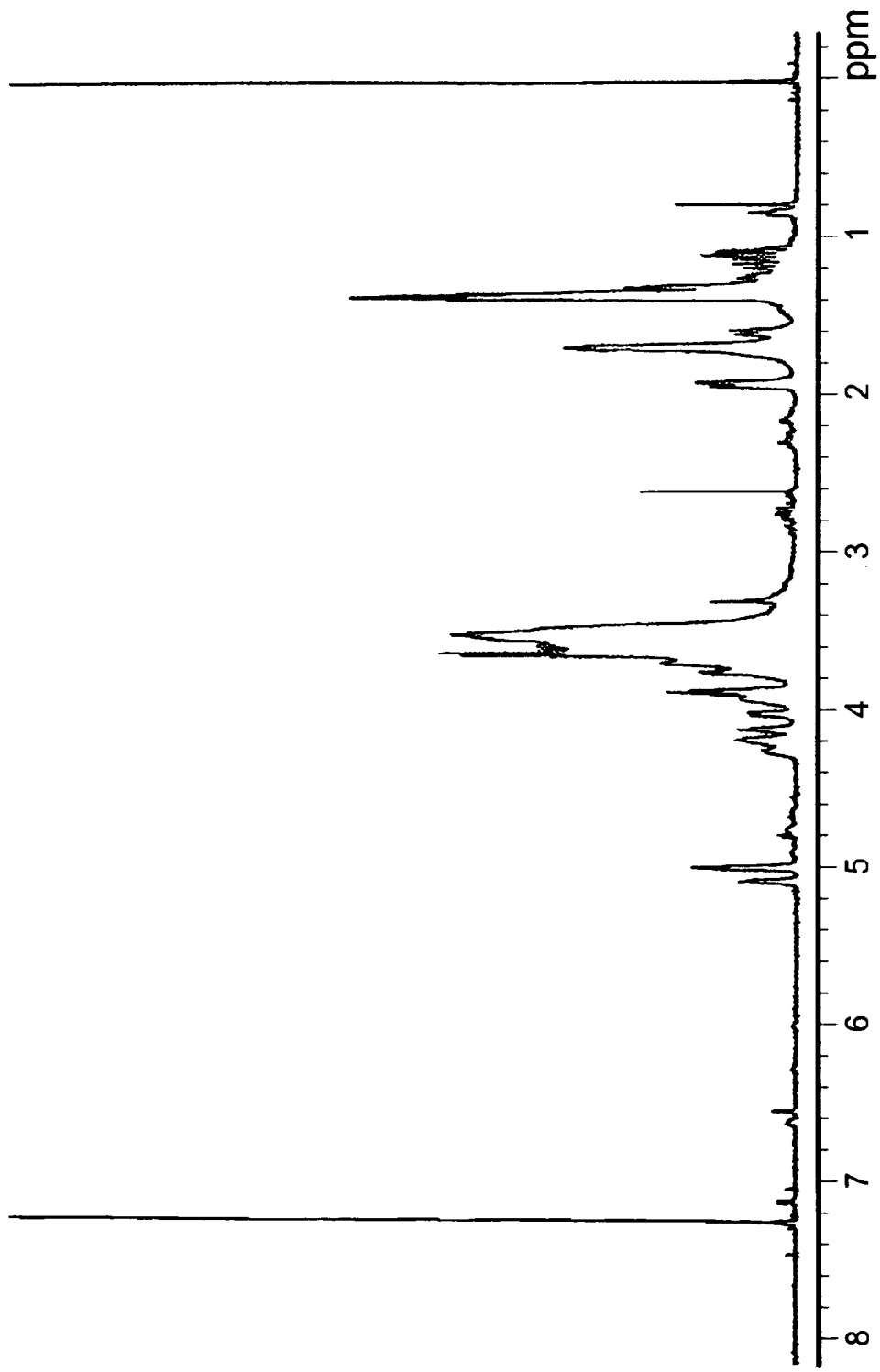
FIG. 24 shows $^1$H NMR of four component copolymer HPG-co-TREDVE-co-folic acid-co-fulvestrant.
Figure 25:
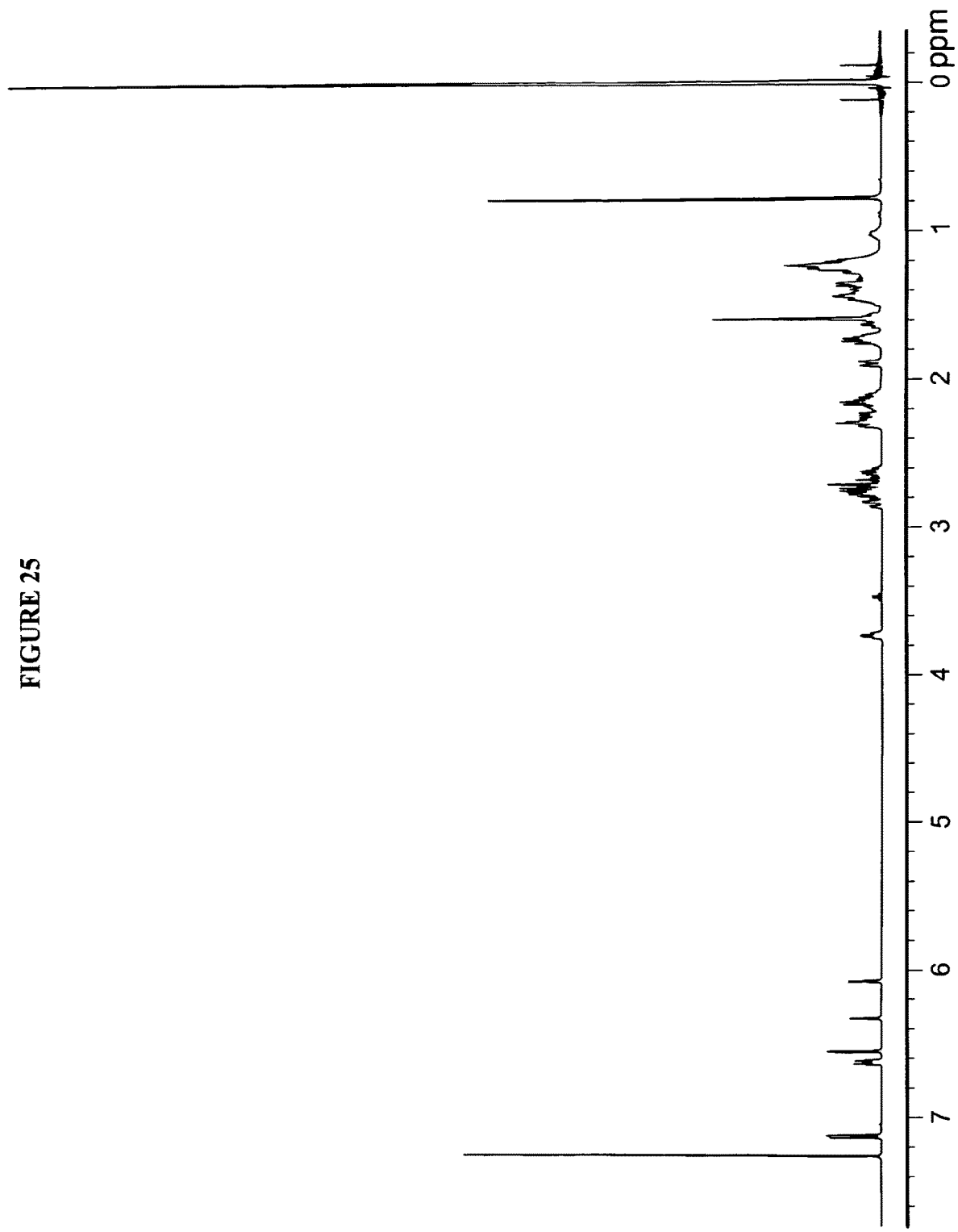
FIG. 25 shows ($S_H$, 500 MHz, CDCL3): fulvestrant.

The LCST was also investigated by measurement of the liquogel solution optical absorption as a function of temperature using UV/Vis spectroscopy and differential scanning calorimetry differential scanning calorimetry (DSC). Scanning the liquogel solution at 500 nm over the temperature range of 0° C. to 43.3° C. (see FIG. 19), the temperature at which the optical absorption rapidly transitions (the LCST) occurs around 35° C. This was also confirmed by a transition at 35.7° C. (see FIG. 20). The heating rate for DSC was 10° C./min.

Example 3

The cytotoxicity of the delivery system (0.09-90 μg/mL) was assessed using fibroid cells. The cells were isolated by enzymatic digestion of fibroid tissue obtained at hysterectomy and cultured in the presence of 10% serum until 80% confluent. The HPGs are less than 3,000 g/mole. Glass transition temperatures are in the sub-ambient range. Viscosity of the polymers were linearly related to concentration in the range between 0.61 and 71.4 g/L. The HPG polymers were derivatized with a linker that was 3:1 methacrylate to lactide and subsequently treated with 60% isopropylacrylamide to afford the final delivery system. After 60 h incubation of the delivery system with primary fibroid cells at 37° C., there was no significant cell death.

Example 4

Figure 16:
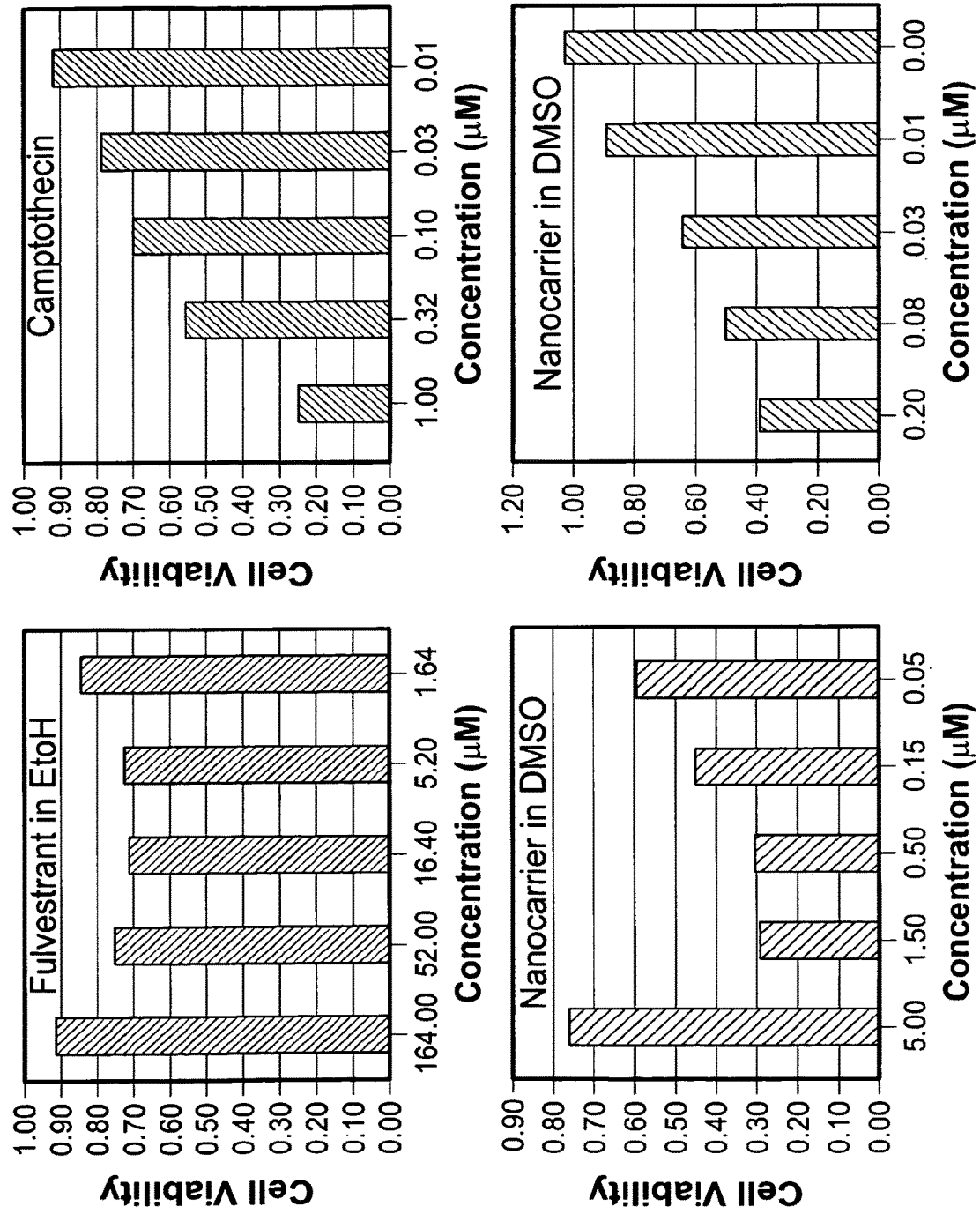
FIG. 16 shows the effects on cell viability.
Figure 17:
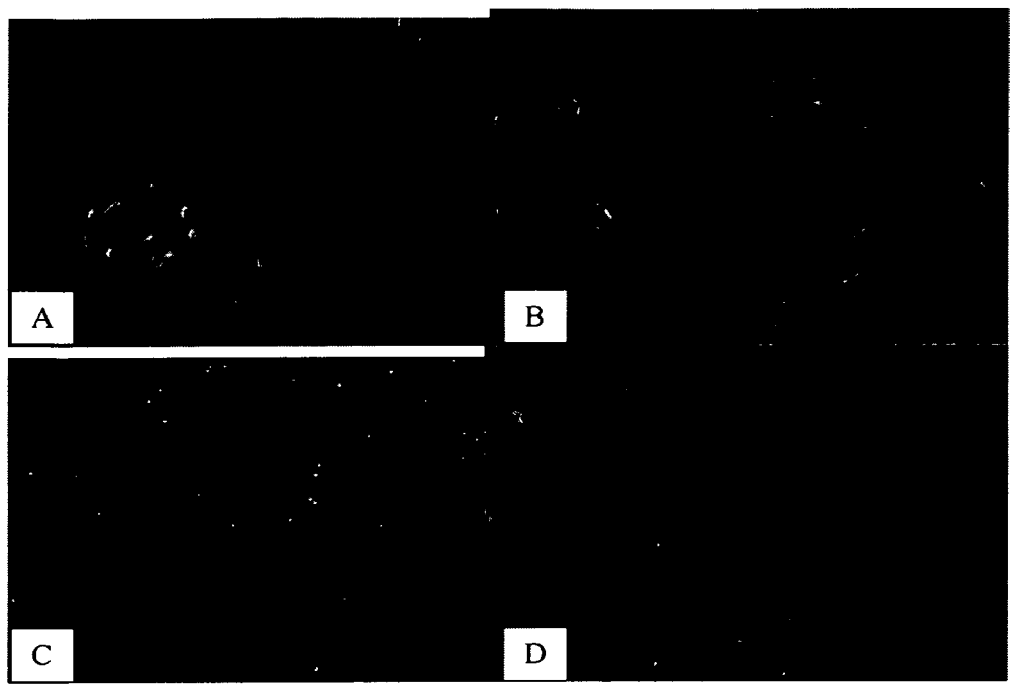
FIG. 17 shows the cytotoxic effect on MCF-7 cells.

The cytotoxic effects of a pH triggered delivery system of fulvestrant, camptothecin or nanocarrier on MCF-7 cells is shown in FIGS. 16 and 17. Comparison of cytotoxic effects by Fulvestrant, Camptothecin and Nanocarrier.

REFERENCES

1. Huang, X.; Misra, G. P.; Vaish, A.; Flanagan, J. M.; Sutermaster, B.; Lowe, T. L., Novel nanogels with both thermoreponsive and thydrolytically degradable properties. *Macromolecules* 2008, 41 (22), 8339-8345.
2. Rubio-Retama, J.; Zafeiropoulos, N. E.; Serafinelli, C.; Rojas-Reyna, R.; Voit, B.; Cabarcos, E. L.; Stamm, M., Synthesis and characterization of thermosensitive PNIPAM microgels covered with superparamagnetic gamma-$Fe_2O_3$ nanoparticles. *Langmuir* 2007, 23 (20), 10280-5.
3. Ruel-Gariepy, E.; Leroux, J. C., In situ-Forming hydrogels-review of temperature-sensitive systems, *European J. of Pharmaceutics and Biopharmaceutics* 2004, 58 409-426.
4. Al-Tahami, K.; Singh, J., Smart polymer based delivery systems for peptides and proteins. *Recent Patents on Drug Delivery & Formulation* 2007, 1, 65-71.

5. Geever, L. M.; Devine, D. M.; Nugent, M. J. D.; Kennedy, J. E.; Lyons, J. G.; Higginbotham, C. L., The synthesis, characterisation, phase behaviour and swelling of temperature sensitive physically crosslinked poly(l-vinyl-2-pyrrolidinone)/poly 1 (N-isopropylacrylamide) hydrogels. *European Polymer Journal* 2006, 42 (1), 69-80.

6. He, C.; Kim, S. W.; Lee, D. S., In situ gelling stimuli-sensitive block copolymer hydrogels for drug delivery. *J. Control. Release* 2008, 127 (3), 189-207.

7. Hacker, M. C.; Klouda, L.; Ma, B. B.; Kretlow, J. D.; Mikos, A. G., Synthesis and characterization of injectable, thermally and chemically gelable, amphiphilic poly(N-isopropylacrylamide)-based macromers. *Biomacromolecules* 2008, 9 (6), 1558-1570.

8. Klouda, L.; Mikos, A. G., Thermoresponsive hydrogels in biomedical applications. *Eur. J. Pharm. Biopharm.* 2008, 68 (1), 34-45.

9. Fujimoto, K. L.; Ma, Z.; Nelson, D. M.; Hashizume, R.; Guan, J.; Tobita, K.; Wagner, W. R., Synthesis, characterization and therapeutic efficacy of a biodegradable, thermoresponsive hydrogel designed for application in chronic infarcted myocardium. *Biomaterials* 2009, 30 (26), 4357-4368.

10. Rzaev, Z. M. O.; Dinçer, S.; Piskin, E., Functional copolymers of N-isopropylacrylamide for bioengineering applications. *Progress in Polymer Science* 2007, 32 (5), 534-595.

11. Li, Z.; Wang, F.; Roy, S.; Sen, C. K.; Guan, J., Injectable, highly flexible, and thermosensitive hydrogels capable of delivering superoxide dismutase. *Biomacromolecules* 2009, 10 (12), 3306-3316.

12. Metters, A. T.; Anseth, K. S.; Bowman, C. N., Fundamental studies of a novel, biodegradable PEG-b-PLA hydrogel. *Polymer* 2000, 41 (11), 3993-4004.

13. Ma, Z.; Nelson, D. M.; Hong, Y.; Wagner, W. R., Thermally responsive injectable hydrogel incorporating methacrylate-polylactide for hydrolytic lability. *Biomacromolecules* 2010, 11 (7), 1873-1881.

14. Kainthan, R. K.; Janzen, J.; Levin, E.; Devine, D. V.; Brooks, D. E., Biocompatibility testing of branched and linear polyglycidol. *Biomacromolecules* 2006, 7 (3), 703-9.

15. Kainthan, R. K.; Muliawan, E. B.; Hatzikiriakos, S. G.; Brooks, D. E., Synthesis, charaterization, and viscoelastic properties of high molecular weight hyperbranched polyglycerols. *Macromolecules* 2006, 39, 7708-7717.

16. Calderon, M.; Quadir, M. A.; Sharma, S. K.; Haag, R., Dendritic polyglycerols for biomedical applications. *Adv. Mater.* 2010, 22 (2), 190-218.

17. Calderon, M.; Quadir, M. A.; Strumia, M.; Haag, R., Functional dendritic polymer architectures as stimuli-responsive nanocarriers. *Biochimie* 2010, 92 (9), 1242-51.

18. Frey, H.; Haag, R., Dendritic polyglycerol: a new versatile biocompatible material *Rev. Mol. Biotechnol.* 2002, 90, 257.

19. Papp, I.; Dernedde, J.; Enders, S.; Haag, R., Modular synthesis of multivalent glycoarchitectures and their unique selectin binding behavior. *Chem. Commun. (Camb.)* 2008, (44), 5851-3.

20. Quadir, M. A.; Radowski, M. R.; Kratz, F.; Licha, K.; Hauff, P.; Haag, R., Dendritic multishell architectures for drug and dye transport. *J. Control. Release* 2008, 132 (3), 289-94.

21. Sunder, A.; Hanselmann, R.; Frey, H.; Mulhaupt, R., Controlled synthesis of hyperbranched polyglyccrols by ring-opening multibranching polymerization. *Macromolecules* 1999, 32, 4240-4246.

22. André, P.; Lacroix-Desmazes, P.; Taylor, D. K.; Boutevin, B., Solubility of fluorinated homopolymer and block copolymer in compressed $CO_2$ *J. Supercritical Fluids* 2006, 37 263-270.

23. Wells, S. L.; Taylor, D.; Adam, M.; DeSimone, J. M.; Farago, B., Study of the association of a diblock copolymer and absorption of an insoluble homopolymer in $CO_2$. *Macromolecules* 2001, 34 (18), 6161-6163.

24. Duncan, R.; Izzo, L., Dendrimer biocompatibility and toxicity. *Advanced Drug Delivery Reviews* 2005, 57 (15), 2215-2237.

25. Kojima, C.; Yoshimura, K.; Harada, A.; Sakanishi, Y.; Kono, K., Temperature-sensitive hyperbranched poly (glycidol)s with oligo(ethylene glycol) monoethers. *Journal of Polymer SciencePart A: Polymer Chemistry* 2010, 48 (18), 4047-4054.

26. Oudshoorn, M. H.; Rissmann, R.; Bouwstra, J. A.; Hennink, W. E., Synthesis and characterization of hyperbranched polyglycerol hydrogels. *Biomaterials* 2006, 27 (32), 5471-9.

27. Feil, H.; Bae, Y. H.; Feijen, J.; Kim, S. W., Effect of comonomer hydrophilicity and ionization on the lower critical solution temperature of N-isopropylacrylamide copolymers. *Macromolecules* 1993, 26 (10), 2496-2500.

28. Schick, M. J.; Fowkes, F. M., *Surface Science Series*. Marcel Dekker.: New York, 1990.

29. Wellons, S. L.; Carey, M. A.; Elder, D. K., Determination of hydroxyl content of polyurethane polyols and other alcohols. *Anal. Chem.* 1980, 52, 7376-7377.

30. Tian, J.; Seery, T. A. P.; Weiss, R. A., Physically cross-linked alkylacrylamide hydrogels: Phase behavior and microstructure. *Macromolecules* 2004, 37 (26), 9994-10000.

31. Takizawa, K.; Nulwala, H.; Hu, J.; Yoshinaga, K.; Hawker, C. J., Molecularly defined (L)-lactic acid oligomers and polymers: Synthesis and characterization. *Journal of Polymer Science Part A: Polymer Chemistry* 2008, 46 (18), 5977-5990.

32. Weir, N. A.; Buchanan, F. J.; Orr, J. F.; Dickson, G. R., Degradation of poly-L-lactide. Part 1: in vitro and in vivo physiological temperature degradation. *Proceedings of the Institution of Mechanical Engineers—Part H—Journal of Engineering in Medicine (Professional Engineering Publishing)* 2004, 218 (5), 307-319.

33. Törmälä, P.; Pohjonen, T.; Rokkanen, P., Bioabsorbable Polymers: materials technology and surgical applications. *Proceedings of the Institution of Mechanical Engineers—Part H—Journal of Engineering in Medicine (Professional Engineering Publishing)* 1998, 212 (2), 101-112.

34. Lee, B. H.; Vernon, B., In situ-gelling, erodible N-Isopropylacrylamide copolymers. *Macromol. Biosci.* 2005, 5 (7), 629-635.

35. Wells, S. L.; Taylor, D.; Adam, M.; DeSimone, J. M.; Farago, B. "Study of the Association of a Diblock Copolymer and Absorption of an Insoluble Homopolymer in $CO_2$", *Macromolecules* 2001, 34(18), 6161-6163.

36. Taylor, D. K. and Ochieng, M. O. "Synthesis, Characterization, Thermoresponse and Degradation of Hyperbranched Polyglycerol based Hydrogel" *Bioconjugates Chem*, 2010, submission.

37. Ulbrich, K., Etrych, T., Chytil, P., Jelinkova, M. & Rihova, B. HPMA copolymers with pH-controlled release of doxorubicin—In vitro cytotoxicity and in vivo antitumor activity. *Journal of Controlled Release* 2003, 87, 33-47.

38. Heller, J., Barr, J., Ng, S. Y., Abdellauoi, K. S. & Gurny, R. Poly(ortho esters): synthesis, characterization, properties and uses. *Advanced Drug Delivery Reviews* 2002, 54, 1015-1039.
39. Murthy, N., Campbell, J., Fausto, N., Hoffman, A. S. & Stayton, P. S. Design and synthesis of pH-responsive polymeric carriers that target uptake and enhance the intracellular delivery of oligonucleotides. *Journal of Controlled Release* 2003, 89, 365-374.
40. Murthy, N., Thng, Y. X., Schuck, S., Xu, M. C. & Frechet, J. M. J. A novel strategy for encapsulation and release of proteins: Hydrogels and microgels with acid-labile acetal cross-linkers. *Journal of the American Chemical Society* 2002, 124, 12398-12399.
41. Gillies, E. R., Goodwin, A. P. & Frechet, J. M. J. Acetals as pH-sensitive linkages for drug delivery. *Bioconjugate Chemistry* 2004, 15, 1254-1263.
42. Neville, D. M., Srinivasachar, K., Stone, R. & Scharff, J. Enhancement of Immunotoxin Efficacy by Acid-Cleavable Cross-Linking Agents Utilizing Diphtheria-Toxin and Toxin Mutants. *Journal of Biological Chemistry* 1989, 264, 14653-14661.
43. Srinivasachar, K. & Neville, D. M. New Protein Cross-Linking Reagents That Are Cleaved by Mild Acid. *Biochemistry* 1989, 28, 2501-2509.
44. Asokan, A. & Cho, M. J. Exploitation of intracellular pH gradients in the cellular delivery of macromolecules. *Journal of Pharmaceutical Sciences* 2002, 91, 903-913.

The invention claimed is:

1. A method of treating a condition or disease, or identifying a disease or condition comprising administering a composition comprising HPG macromers, a crosslinker, a biodegradable component and a thermoresponsive component to a subject in need hereof, wherein the condition or disease is a uterine fibroid.

2. The method according to claim 1, wherein the composition comprises hyperbranched polyglycerol (HPG), a crosslinker, a biodegradable component, a thermoresponsive component, a pH responsive component, N-isopropylacrylamide, and at least one drug or therapeutic agent.

3. The method according to claim 1, wherein the composition further comprises a therapeutic agent.

4. The method according to claim 1, wherein the composition is a liquogel or a nanocarrier.

5. The method according to claim 1, wherein the composition further comprises a pH responsive polymer.

6. The method according to claim 1, wherein the crosslinker is an acrylate group.

7. The method according to claim 1, wherein the biodegradable component is selected from poly (lactic acid), lactide poly (trimethylene carbonate), poly ($\varepsilon$-caprolactone), hyaluronic acid, gelatin, peptides and collagen.

8. The method according to claim 1, wherein the thermoresponsive component is selected from N-alkyl acrylamide and polyethylene glycol.

9. The method according to claim 1, wherein the composition comprises acrylic acid, poly(lactic acid), N-isopropylacrylamide, and hyperbranched polyglycerol macromer.

10. The method according to claim 1, wherein the composition comprises methyacrylated hyperbranched polyglycerol (HPG-MA), N-isopropylacrylamide (NI-PAAm), hydroxyethyl methacrylate-polylactide (HEMA-PLA) and acrylic acid (AAc).

11. The method according to claim 1, wherein the composition is administered by injection.

* * * * *